US009988670B2

(12) United States Patent
Afonina et al.

(10) Patent No.: US 9,988,670 B2
(45) Date of Patent: Jun. 5, 2018

(54) METHODS AND COMPOSITIONS FOR DETECTING ANTIBIOTIC RESISTANT BACTERIA

(71) Applicant: ELITechGroup B.V., Spankeren (NL)

(72) Inventors: Irina A. Afonina, Mill Creek, WA (US); Yevgeniy S. Belousov, Mill Creek, WA (US)

(73) Assignee: ELITECHGROUP B.V., Spankeren (NL)

(*) Notice: Subject to any disclaimer, the term of this patent is extended or adjusted under 35 U.S.C. 154(b) by 84 days.

(21) Appl. No.: 14/964,716

(22) Filed: Dec. 10, 2015

(65) Prior Publication Data
US 2016/0168625 A1    Jun. 16, 2016

Related U.S. Application Data

(60) Provisional application No. 62/091,007, filed on Dec. 12, 2014.

(51) Int. Cl.
C12Q 1/68    (2018.01)

(52) U.S. Cl.
CPC .......... C12Q 1/6806 (2013.01); C12Q 1/689 (2013.01); C12Q 1/6853 (2013.01); C12Q 2600/112 (2013.01); C12Q 2600/156 (2013.01); Y02A 50/451 (2018.01)

(58) Field of Classification Search
CPC .......... C12Q 1/6853; C12Q 2525/161; C12Q 2561/113; C12Q 2563/107; C12Q 2565/1015; C12Q 2565/107; C12Q 1/6806; C12Q 1/689; C12Q 2600/112; C12Q 2600/156
USPC .............. 435/6.11, 6.12; 506/9, 16
See application file for complete search history.

(56) References Cited

U.S. PATENT DOCUMENTS

| | | |
|---|---|---|
| 3,128,179 A | 4/1964 | Kendall et al. |
| 3,194,805 A | 7/1965 | Brooker et al. |
| 3,996,345 A | 12/1976 | Ullman et al. |
| 4,351,760 A | 9/1982 | Khanna et al. |
| 4,415,732 A | 11/1983 | Caruthers et al. |
| 4,458,066 A | 7/1984 | Caruthers et al. |
| 4,683,195 A | 7/1987 | Mullis et al. |
| 4,739,044 A | 4/1988 | Stabinsky |
| 4,757,141 A | 7/1988 | Fling et al. |
| 4,965,188 A | 10/1990 | Mullis et al. |
| 4,997,928 A | 3/1991 | Hobbs |
| 5,187,288 A | 2/1993 | Kang et al. |
| 5,188,934 A | 2/1993 | Menchen et al. |
| 5,227,487 A | 7/1993 | Haugland et al. |
| 5,231,191 A | 7/1993 | Woo et al. |
| 5,248,782 A | 9/1993 | Haugland et al. |
| 5,304,645 A | 4/1994 | Klein et al. |
| 5,419,966 A | 5/1995 | Reed et al. |
| 5,433,896 A | 7/1995 | Kang et al. |
| 5,442,045 A | 8/1995 | Haugland et al. |
| 5,508,178 A | 4/1996 | Rose et al. |
| 5,512,677 A | 4/1996 | Chern et al. |
| 5,538,848 A | 7/1996 | Livak et al. |
| 5,556,959 A | 9/1996 | Brush et al. |
| 5,583,236 A | 12/1996 | Brush |
| 5,585,481 A | 12/1996 | Arnold et al. |
| 5,696,251 A | 12/1997 | Arnold et al. |
| 5,736,626 A | 4/1998 | Mullah et al. |
| 5,801,155 A | 9/1998 | Kutyavin et al. |
| 5,808,044 A | 9/1998 | Brush et al. |
| 5,852,191 A | 12/1998 | Karandikar et al. |
| 5,925,517 A | 7/1999 | Tyagi et al. |
| 5,942,610 A | 8/1999 | Nelson et al. |
| 5,986,086 A | 11/1999 | Brush et al. |
| 5,994,056 A | 11/1999 | Higuchi |
| 6,020,481 A | 2/2000 | Benson et al. |
| 6,162,931 A | 12/2000 | Gee et al. |

(Continued)

FOREIGN PATENT DOCUMENTS

| | | |
|---|---|---|
| CN | 101948920 B | 1/2011 |
| CN | 102899414 A * | 1/2013 |

(Continued)

OTHER PUBLICATIONS

The International Search Report and Written Opinion issued by the European Patent Office dated Jun. 21, 2016 for the copending PCT patent application No. PCT/US2015/064886.

Bengtsson et al., "A New Minor Groove Binding Asymmetric Cyanine Report Dye for Real-Time PCR", Nucleic Acids Research, 2003, pp. 1-5, vol. 31, No. 8, e45.

Bolli et al., "Watson-Crick Base-Paring Properties of Bicyclo-DNA", Nucleic Acids Research, 1996, pp. 4660-4667, vol. 24, No. 23.

(Continued)

Primary Examiner — Janet L Epps-Smith
(74) Attorney, Agent, or Firm — Jackson Walker LLP

(57) ABSTRACT

Primers and probes specific to genes encoding carbapenem-resistant Enterobacteriaceae (CREs) that include KPC (*Klebsiella pneumoniae* carbapenemase), NDM-1 (New Delhi Metallo-beta-lactamase), VIM (Verona Integron-Mediated Metallo-β-lactamase), IMP-type carbapenemase and OXA 48 (oxacillinase), that cause resistance in Enterobacteriaceae bacteria, are described herein, with methods and kits for using these primers and probes to detect target nucleic acids. In the methods described, nucleic acids present in a clinical or test sample obtained from a biological sample or tissue suspected of containing the the NDM1, KPC, IMP, VIM and OXA genes are amplified and corresponding sequences for the NDM1, KPC, IMP, VIM and OXA genes are detected. The amplified nucleic acid can be detected by a variety of state of the art methods, including fluorescence resonance energy transfer (FRET), radiolabels, enzyme labels, and the like.

26 Claims, 12 Drawing Sheets

(56) References Cited

U.S. PATENT DOCUMENTS

| | | | |
|---|---|---|---|
| 6,180,295 | B1 | 1/2001 | Helber et al. |
| 6,217,121 | B1 | 4/2001 | Mollet |
| 6,221,604 | B1 | 4/2001 | Upadhya et al. |
| 6,312,894 | B1 | 11/2001 | Hedgpeth et al. |
| 6,653,473 | B2 | 11/2003 | Reed et al. |
| 6,683,173 | B2 | 1/2004 | Dempcy et al. |
| 6,727,356 | B1 | 4/2004 | Reed et al. |
| 6,790,945 | B2 | 9/2004 | Lukhtanov et al. |
| 6,905,848 | B2 | 6/2005 | Hanson et al. |
| 6,949,367 | B1 | 9/2005 | Dempcy et al. |
| 6,972,339 | B2 | 12/2005 | Lukhtanov et al. |
| 7,045,610 | B2 | 5/2006 | Dempcy et al. |
| 7,205,105 | B2 | 4/2007 | Afonina et al. |
| 7,319,022 | B1 | 1/2008 | Mahoney et al. |
| 7,381,818 | B2 | 6/2008 | Lokhov et al. |
| 7,582,739 | B2 | 9/2009 | Lukhtanov et al. |
| 7,662,942 | B2 | 2/2010 | Reed et al. |
| 7,671,218 | B2 | 3/2010 | Lukhtanov et al. |
| 7,759,126 | B2 | 7/2010 | Lokhov et al. |
| 7,767,834 | B2 | 8/2010 | Lukhtanov et al. |
| 7,790,385 | B2 | 9/2010 | Kutyavin et al. |
| 7,968,292 | B2 | 6/2011 | Whiteford et al. |
| 8,163,910 | B2 | 4/2012 | Lukhtanov |
| 8,410,255 | B2 | 4/2013 | Cook et al. |
| 2005/0118623 | A1 | 6/2005 | Belousov et al. |
| 2007/0048758 | A1 | 3/2007 | Lokhov et al. |
| 2009/0031780 | A1 | 2/2009 | Bandou et al. |
| 2009/0163382 | A1* | 6/2009 | Oh .................. C12Q 1/689 506/17 |
| 2011/0190170 | A1 | 8/2011 | Sampath et al. |
| 2012/0129180 | A1* | 5/2012 | Kirveskari .......... C12Q 1/689 435/6.12 |
| 2012/0244535 | A1 | 9/2012 | Vorobiev et al. |
| 2012/0245219 | A1 | 9/2012 | Khvorova et al. |

FOREIGN PATENT DOCUMENTS

| | | |
|---|---|---|
| CN | 102899414 A | 1/2013 |
| CN | 102242197 B | 5/2013 |
| CN | 102534014 B | 2/2014 |
| EP | 1408366 A2 | 4/2004 |
| KR | 20130017818 A | 2/2013 |
| WO | 1999/37085 A2 | 7/1999 |
| WO | 2010/130882 A1 | 11/2010 |
| WO | 2012/023054 A2 | 2/2012 |
| WO | 2013/048583 A2 | 4/2013 |

OTHER PUBLICATIONS

Capaldi et al., "Signal Amplification Through Nucleotide Extension and Excision on a Dendritic DNA Platform", Nucleic Acids Research, 2000, pp. 1-8, vol. 28, No. 7, e21.

Dreier et al., "Use of Bacteriophage MS2 as an Internal Control in Viral Reverse Transcroption-PCR Assays", Journal of Clinical Microbiology, 2005, pp. 4551-4557, vol. 43, No. 9.

Georgopapadakou, "Prospects for New Antibacterials; Can We Do Better?", Expert Opinion Investig. Drugs, 2014, pp. 145-148, vol. 23, No. 2.

Giusti et al., "Synthesis and characterization of 5'-fluorescent-dye-labeled oligonucleotides", PCR Methods and Applications, Genome Research, 1993, pp. 223-227, vol. 2.

Hoorfar et al., "Practical Considerations in Design of Internal Amplification Controls for Diagnostic PCR Assays," Journal of Clinical Microbiology, 2004, pp. 1863-1868, vol. 42, No. 5.

Holton et al., "Appropriate prescribing of oral beta-lactam antibiotics", American Family Physician, 2000, pp. 611-620, vol. 62, No. 3.

Kutyavin et al., "3'-Minor Groove Binder-DNA Probes Increase Sequence Specificity at PCR Extension Temperatures", Nucleic Acids Research, 2000, pp. 655-661, vol. 28, No. 2.

Mullis et al., "Specific Enzymatic Amplification of DNA In Vitro: The Polymerase Chain Reaction", Cold Spring Harb. Symp. Quant. Biol., 1986, pp. 263-273, vol. 51.

Nelson et al., "Bifunctional Oligonucleotide Probes Synthesized Using a Novel CPG Support are able to Detect Single Base Pair Mutations", Nucleic Acids Research, 1989. pp. 7187-7194, vol. 17, No. 18.

Nielsen et al., "Sequesnce-Selective Recognition of DNA by Strand Displacement with a Thymine-Substituted Polyaminde", Science, 1991, pp. 1497-1500, vol. 254, No. 5037.

Niemz et al., "Point-of-care Nucleic Acid Testing for Infectious Diseases", Trends in Biotechnology, 2011, pp. 240-250, vol. 29, No. 5.

Papagiannitsis et al., "Characterization of Metallo-β-Lactamase VIM-27, an A575 Mutant of VIM-1 Associated with Klebsiella pneumoniae ST147", Antimicrobial Agents and Chemotherapy, 2011, pp. 3570-3572, vol. 55, No. 7.

Perez et al., "Carbapenem-resistant Enterobacteriaceae: A Menace to our most vulnerable patients", Cleveland Clinic Journal of Medicone, 2013, pp. 225-233, vol. 80, No. 4.

Picard et al., "Internal control for nucleic acid testing based on the use of purified *Bacillus atrophaeus* subsp. *globigii* spores", Journal of Clinical Microbiology, 2009, pp. 751-757, vol. 47, No. 3.

Poirel et al., "Genetic Features of the Widespead Plasmid Coding for the Carbapenemase OXA-48", Antimicrob. Agents Chemother., 2012, pp. 559-562, vol. 56 No. 1.

Potron et al., "Characterization of OXA-181, a Carbapenem-Hydrolyzing Class D β-Lactamase from Klebsiella pneumoniae" Antimicrobial Agents and Chemotherapy, 2011, pp. 4896-4899, vol. 55, No. 10.

Reddy et al., "Synthetic DNA Minor Groove-Binding Drugs", Pharmacology & Therapeutics, 1999, pp. 1-50, vol. 84.

Samuelsen et al., "Identification of Enterobacteriaceae isolates with OXA-48 and coproduction of OXA-181 and NDM-1 in Norway", J Antimicrob Chemother., 2013, pp. 1682-1685, vol. 68, No. 7.

Sproat et al. "The synthesis of protected 5'-mercapto-2', 5'-dideoxyribonucleoside-3'-0-phosphorainidites; uses of 5'-mercapto-oligodeoxyribonucleotides", Nucleic Acids Research, 1987, pp. 4837-4848, vol. 15, No. 12.

Users Manual Model 392 and 394 Polynucleotide Synthesizers, 1991, pp. 6-1 through 6-22, Applied Biosystems, Part No. 901237.

Walker et al., "Progress in the Design of DNA Sequence-Specific Lexitropsins", Biopolymers, 1997, pp. 323-334, vol. 44, No. 4.

Wemmer et al. "Targeting the Minor Groove of DNA", Current Opinion in Structured Biology, 1997, pp. 355-361, vol. 7.

Yigit et al., "Novel Carbapenem-Hydrolyzing β-Lactamase, KPC-1, from a Carbapenem-Resistant Strain of Klebsiella pneumoniae" Antimicrobial Agents and Chemotherapy, 2001, pp. 1151-1161, vol. 45, No. 4.

Yong et al., "Characterization of a New Metallo-β-Lactamase Gene, blaNDM-1, and a Novel Erythromycin Esterase Gene Carried on a Unique Genetic Structure in Klebsiella pneumoniae Sequence Type 14 from India" Antimicrobial Agents and Chemotherapy, 2009, pp. 5046-5054, vol. 53, No. 12.

Zimmer et al., "Nonintercalating DNA-Binding Ligands: Specificity of the Interaction and their Use as Tools in Biophysical, Biochemical and Biological Investigations of the Genetic Material", Prog. Biophys. Molec. Bio., 1986, pp. 31-112, vol. 47.

Zuckermann et al., "Efficient methods for attachment of thiol specific probes to the 3'-ends of synthetic oligodeoxyribonucleotides", Nucleice Acids Research, 1987, pp. 5305-5321, vol. 15, No. 13.

The International Preliminary Report on Patentability issued by the International Bureau of WIPO dated Jun. 22, 2017 for International PCT application No. PCT/US2015/064886.

The Communication pursuant to Rules 161(1) and 162 EPC issued by the European Patent Office dated Aug. 1, 2017 for the co-pending European patent application No. 158166355.

The Invitation to Pay Additional Fees and, Where Applicable, Protest Fee, issued by EPO on Apr. 11, 2016 for the corresponding PCT Application No. PCT/US2015/064886.

Yong et al., "Characterization of a New Metallo-β-Lactamase Gene, bla(NDM-1), and a novel erythromycin esterase gene carried on a unique genetic structure in Klebsiella pneumoniae sequence type 14 from India", Antimicrobial Agents and Chemotherapy, Sep. 2009, pp. 5046-5054, vol. 53, No. 12.

(56) References Cited

OTHER PUBLICATIONS

Timmons et al., "Primers with 5' Flaps Improve the Efficiency and Sensitivity of Multiplex PCR Assays for the Detection of *Salmonella* and *Escherichia coli* O 157:H7", Journal of Food Protection, 2013, pp. 668-673, vol. 76, No. 4.

Kutyavin et al., "3'-Minor groove binder-DNA probes increase sequence specificity at PCR extension temperatures", Nucleic Acids Research, 2000, pp. 655-661, vol. 28, No. 2, Oxford University Press.

* cited by examiner (a)

(b)

(a)

(b)

METHODS AND COMPOSITIONS FOR DETECTING ANTIBIOTIC RESISTANT BACTERIA

This application claims priority to U.S. Provisional Patent Application Ser. No. 62/091,007, entitled "Methods and Compositions for Detecting Antibiotic Resistant Bacteria," filed Dec. 12, 2014, the entire content of which is hereby incorporated by reference.

BACKGROUND

This disclosure relates to bacterial diagnostics and more particularly to the detection of carbapenemase resistant genes that cause carbapenemase-resistance in bacteria.

β-Lactam antibiotics (beta-lactam antibiotics) are a broad class of antibiotics, consisting of all antibiotic agents that contain a β-lactam ring in their molecular structures. This includes penicillin derivatives (penams), cephalosporins (cephems), monobactams, and carbapenems. (Holten K B, Onusko E M (August 2000)). Most β-lactam antibiotics work by inhibiting cell wall biosynthesis in the bacterial organism and are the most widely used group of antibiotics. β-Lactam antibiotics are indicated for the prophylaxis and treatment of bacterial infections caused by susceptible organisms. At first, β-lactam antibiotics were mainly active only against Gram-positive bacteria, yet the recent development of broad-spectrum β-lactam antibiotics active against various Gram-negative organisms has increased their usefulness.

Bacterial resistance to antibacterial drugs has been increasing relentlessly over the past two decades. This includes common residents of the human body: *Staphylococcus aureus* (methicillin resistant or MRSA) *Enteroccus faecalis* and *E. faecium* (vancomycin resistant or VRE): Enterobacteriaceae (multiresistant, carbapenems included or CRE). It also includes environmental, opportunistic, but intrinsically multiresistant species: *Pseudomonas aeruginosa* and *Acinetobacter baumannii*. (Georgopapadakou (2014)).

CRE, which stands for carbapenem-resistant Enterobacteriaceae, are a family of bacteria that are difficult to treat because they have high levels of resistance to antibiotics. *Klebsiella* species and *Escherichia coli* (*E. coli*) are examples of Enterobacteriaceae, a normal part of the human gut bacteria that can become carbapenem-resistant. Types of CRE are sometimes known as KPC (*Klebsiella pneumoniae* carbapenemase) and NDM-1 (New Delhi Metallo-beta-lactamase). KPC and NDM-1 are enzymes that break down carbapenems and make them ineffective. Both of these enzymes, as well as the enzyme VIM (Verona Integron-Mediated Metallo-β-lactamase) have also been reported in *Pseudomonas*. The most common CREs are KPC, VIM, NDM, IMP (IMP-type carbapenemase) and OXA 48. Ongoing global dissemination of $bla_{OXA\text{-}48\text{-}like}$, as well as the coexistence of $bla_{NDM\text{-}1}$ and $bla_{OXA\text{-}181}$ in a single *K. pneumoniae* strain have been documented.

Primers and probes have previously been described for NDM1 (US20120129180A1, WO2012023054A2), KPC (U.S. Pat. No. 7,968,292, US20120129180A1, US20110190170A1 and WO 2013/078565), IMP (US20120129180A1, US 20090163382 and US20090317807), VIM (US 20090163382, US20120129180 and US20090317807) and OXA (US20090163382A1, US20120129180A1 and U.S. Pat. No. 6,905,848). Multiplex analysis by melting curve analysis using a single dye was reported in US Application NO: 20120129180A1. U.S. Pat. No. 8,124,382 discloses multiplex PCR of tem, shy, ctx-m-1, ctx-m-9, mox, cit, dha, ebc and fox. Amplified targets were detected with a universal-labeled TAMRA dye in array format. US Application 20090163382 discloses the multiplexing of multiple amplified targets with immobilized capture probes on microarrays, and fluorescence emitted from the microarrays was measured.

There exists a clinical need for the rapid detection of the carriers of antibiotic resistant carbapenem-resistant Enterobacteriaceae of the NDM1, KPC, IMP, VIM and OXA genes having higher clinical prevalence rates.

SUMMARY

The present disclosure relates to primers and probes specific to the genes encoding CREs that includes KPC (*Klebsiella pneumoniae* carbapenemase), NDM-1 (New Delhi Metallo-beta-lactamase), VIM (Verona Integron-Mediated Metallo-β-lactamase), IMP-type carbapenemase and OXA 48 (oxacillinase) that cause resistance in Enterobacteriaceae bacteria.

More specifically, the present disclosure relates to primers and probes for the detection of genes encoding certain CREs in samples including biological samples (e.g., rectal swabs). The present invention discloses primers and probes to identify the family of specific beta lactamases producers that carry antibiotic resistance genetic markers in clinical isolates of preferably gram negative bacteria. Specific primers and probes to amplify and detect NDM1, KPC, IMP, VIM and OXA resistance-encoding genes that are disclosed in the primer and probe sequences herein. In the methods described, nucleic acids present in a clinical or test sample obtained from a biological sample or tissue suspected of containing the NDM1, KPC, IMP, VIM or OXA genes are amplified and corresponding sequences for NDM1, KPC, IMP, VIM and OXA are detected. The amplified nucleic acid can be detected by a variety of state of the art methods, including fluorescence resonance energy transfer (FRET), radiolabels, enzyme labels, and the like. The amplified nucleic acids can also be detected by any combination of detection techniques which may include hybridization detection probes.

One embodiment pertains to a method for detecting NDM1, KPC, IMP, VIM and OXA in a biological sample from an individual. Other embodiments provide oligonucleotide primers and probes comprising nucleotide sequences characteristic of NDM1, KPC, IMP, VIM and OXA gene sequences. The method includes performing at least one cycling step of amplification and hybridization. The amplification step includes contacting the sample nucleic acid with one or more pairs of primers to produce amplification product if any of the NDM1, KPC, IMP, VIM and OXA nucleic acid is present. The preferred primers target specific regions of the NDM1, KPC, IMP, VIM and OXA gene of a resistant organism. The oligonucleotide probes detect the amplified target directly or indirectly. The most preferred oligonucleotide probe is a 5'-minor groove binder-fluorophore-oligonucleotide-quencher-3' conjugate that fluoresces on hybridization to its complementary amplified target (see U.S. Pat. Nos. 7,381,818 and 7,759,126). In another embodiment the preferred oligonucleotide probe is a 3'-minor groove binder-quencher-oligonucleotide-fluorophore-3' conjugate that fluoresces on hybridization to its complementary amplified target when cleaved by 5'-endonuclease activity (see Kutyavin et al. (2000)).

In an embodiment, the NDM1, KPC, IMP, VIM and OXA genes are amplified and detected in a single real-time amplification reaction using fluorescent detection. In a preferred method, the CRE gene targets are detected in the presence of an internal control.

In a further embodiment, the probes specific for IMP, VIM and NDM1 genes are labeled with the same fluorophore, while the probes specific for the KPC, OXA and internal control targets are respectively labeled with three different fluorophores.

Kits are also provided for the detection of NDM1, KPC, IMP, VIM and OXA genes in biological samples comprising at least one annealing oligonucleotide primer reagent specific for the amplification of NDM1, KPC, IMP, VIM or OXA sequences and comprising at least one oligonucleotide probe specific for the detection of NDM1, KPC, IMP, VIM or OXA sequences.

The method further includes detecting of the presence or absence of a fluorescent signal (e.g., a signal resulting from FRET) of the hybridization probes of the invention. The presence of the fluorescent signals usually indicates the presence of NDM1, KPC, IMP, VIM or OXA gene sequences in the biological sample, while the absence of signal usually indicates the absence of NDM1, KPC, IMP, VIM or OXA gene sequences in the biological sample. In one embodiment the probes detecting NDM1, KPC, IMP, VIM and OXA gene sequences are labeled with more than one different fluorescent dyes.

The method can additionally include determining the melting temperature profile between the probe and the amplification product. The melting curve further confirms the presence or absence of gene sequences, with mismatch(es) in the probe sequence area. In further embodiment the melting temperature profile between probe and amplification product is measured at more than one fluorescent emission wavelength.

The primers and probes of the invention allow the specific, sensitive, and rapid detection of NDM1, KPC, IMP, VIM and OXA gene sequences that have higher clinical prevalence rates.

DETAILED DESCRIPTION

I. General

Figure 1:
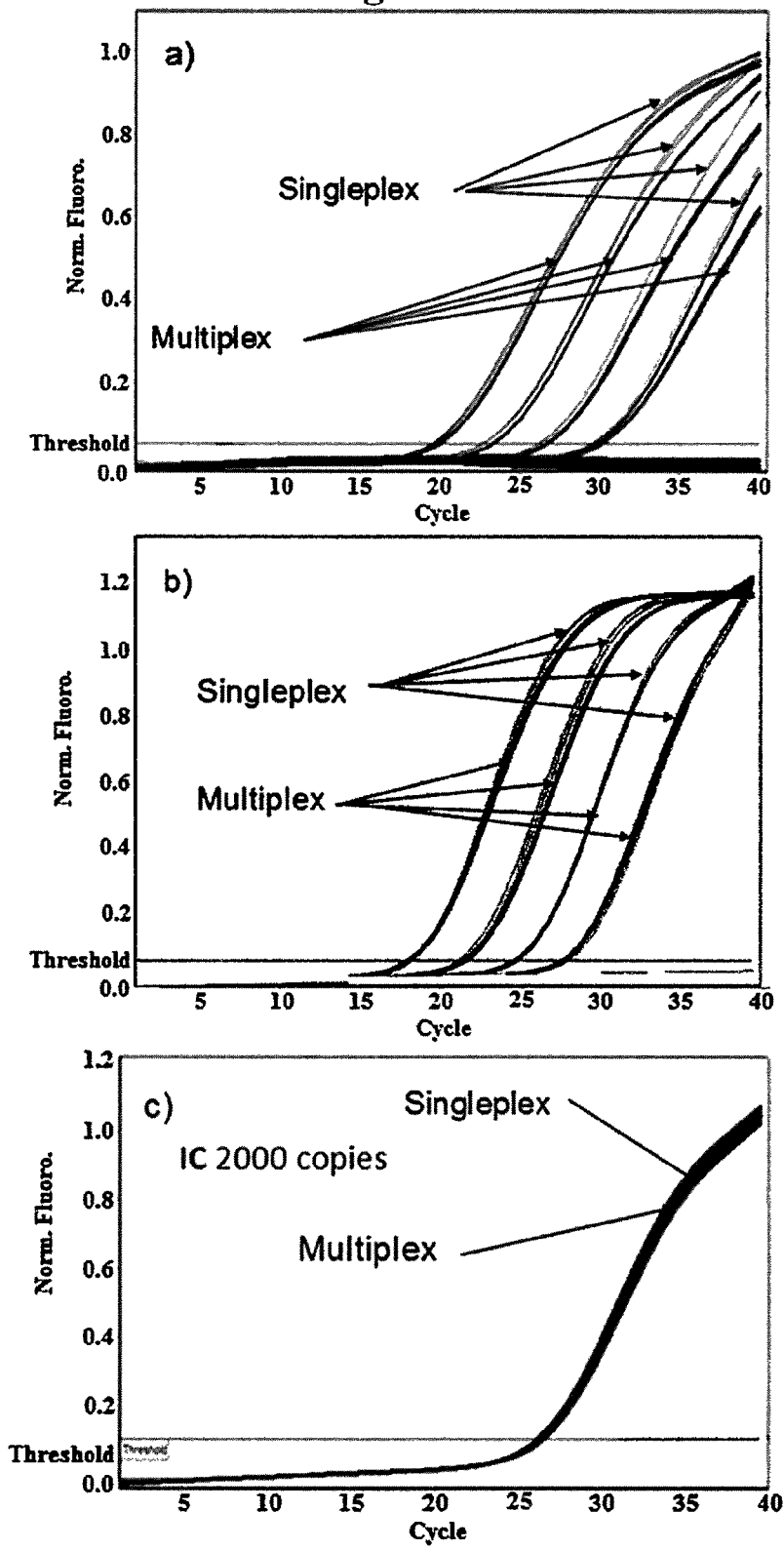
FIG. 1 shows (a) the real-time PCR detection of OXA 48 and 181 targets with a TaqMan probe having SEQ ID NO: 26 in singleplex and multiplex, (b) the real-time PCR detection of OXA 48 and 181 targets with a Pleiades probe having SEQ ID NO: 27 in singleplex and multiplex with an internal control (IC), and (c) the real-time PCR detection of 2000 copies of IC with and without OXA 48 and 181 targets.

The present disclosure provides primers and probes for use in methods for the specific amplification and/or detection of nucleic acid gene sequences encoding certain enzymes, namely KPC (*Klebsiella pneumoniae* carbapenemase), NDM-1 (New Delhi Metallo-beta-lactamase), VIM (Verona Integron-Mediated Metallo-β-lactamase), IMP-type carbapenemase and OXA (oxacillinase).

II. Definitions

The term "CRE" as used herein refers to carbapenem-resistant Enterobacteriaceae, a family of bacteria that are difficult to treat because they have high levels of resistance to antibiotics. Enterobacteriacea bacteria include *Klebsiella*, *Pseudomonas* and *Escherichia coli* (*E. coli*) species that can become carbapenem-resistant.

The terms "KPC", "NDM-1", "VIM", "IMP" and "OXA", the CRE gene targets, as used herein, refer to KPC (*Klebsiella pneumoniae* resistant carbapenemase), NDM-1 (New Delhi Metallo-beta-lactamase), VIM (Verona Integron-Mediated Metallo-β-lactamase), IMP-type carbapenemase and OXA 48 (oxacillinase), respectively. Additionally, the term "OXA" refers to the bla$_{OXA\text{-}48}$ and its derivative bla$_{OXA181}$ gene targets.

A "sample" as used herein refers to a sample of any source which is suspected of containing NDM1, KPC, IMP, VIM or OXA nucleic acids. These samples can be tested by the methods described herein. A sample can be from a laboratory source or from a non-laboratory source. A sample may be suspended or dissolved in liquid materials such as buffers, extractants, solvents, and the like. Samples also include biological samples such as animal and human tissue or fluids such as whole blood, blood fractions, serum, plasma, cerebrospinal fluid, lymph fluids, milk, urine, various external secretions of the respiratory, intestinal, and genitourinary tracts, tears, and saliva; and biological fluids such as cell extracts, cell culture supernatants, fixed tissue specimens, and fixed cell specimens. Samples include nasopharyngeal or throat swabs, stools, or rectal swabs. Biological samples may also include sections of tissues such as biopsy and autopsy samples or frozen sections taken for histologic purposes. A biological sample is obtained from any mammal including, e.g., a human.

The terms "flap primer" or "overhang primer" refer to a primer comprising a 5' sequence segment non-complementary to a target nucleic acid sequence (e.g., NDM1, KPC, IMP, VIM or OXA nucleic acid sequence) and a 3' sequence segment complementary to the target nucleic acid sequence (e.g., NDM1, KPC, IMP, VIM or OXA nucleic acid sequence). The flap primers of the invention are suitable for primer extension or amplification of the target nucleic acid sequences (e.g., NDM1, KPC, IMP, VIM or OXA nucleic acid sequences).

The term "overhang sequence" refers to a non-complementary adapter, flap, or overhang sequence in a primer. "Non-complementary" sequences do not bind to a target sequence under amplification conditions. The flap portion of a flap primer can comprise nucleotides that are complementary to the target sequence provided that the three nucleotides immediately 5' to the portion of the flap are not complementary to the target sequence.

The term "fluorescent generation probe" refers either to a) an oligonucleotide having an attached minor groove binder, fluorophore, and quencher or b) a DNA binding reagent. The probes may comprise one or more non-complementary or modified nucleotides (e.g., pyrazolopyrimidines as described herein below) at any position including, e.g., the 5' end. In some embodiments, the fluorophore is attached to the modified nucleotide.

The term "modified bases" refers to those bases that differ from the naturally-occurring bases (adenine, cytosine, guanine, thymine, and urasil) by addition or deletion of one or more functional groups, differences in the heterocyclic ring structure (i.e., substitution of carbon for a heteroatom, or vice versa), and/or attachment of one or more linker arm structures to the base. Preferred modified nucleotides are those based on a pyrimidine structure or a purine structure, with the latter more preferably being 7 deazapurines and their derivatives and pyrazolopyrimidines (described in U.S. Pat. No. 7,045,610); and also described in U.S. Pat. No. 6,127,121. Preferred modified bases are 5-substituted pyrimidines and 3-substituted pyrazolopyrimidines. Examples of preferred modified bases are 6-amino-1H-pyrazolo[3,4-d]pyrimidin-4(5H)-one (PPG or Super G®), 4-amino-1H-pyrazolo[3,4-d]pyrimidine, 1H-pyrazolo[5,4-d]pyrimidin-4(5H)-6(7H)-dione, 6-amino-3-prop-1-ynyl-5-hydropyrazolo[3,4-d]pyrimidine-4-one, 6-amino-3-(3-hydroxyprop-1-ynyl)-5-hydropyrazolo[3,4-d]pyrimidine-4-one, 6-amino-3-(3-aminoprop-1-ynyl)-5-hydropyrazolo[3,4-d]pyrimidine-4-one, 4-amino-3-(prop-1-ynyl)pyrazolo[3,4-d]pyrimidine, 4-amino-3-(3-hydroxyprop-1-ynyl) pyrazolo[3,4-d]pyrimidine, 4-amino-3-(3-aminoprop-1-ynyl)pyrazolo[3,4-d]pyrimidine, 3-prop-1-ynyl-4,6-diaminopyrazolo[3,4-d]pyrimidine, 2-(4,6-diaminopyrazolo[3,4-d]pyrimidin-3-yl)ethyn-1-ol, 3-(2-aminoethynyl) pyrazolo[3,4-d]pyrimidine-4,6-diamine, 5-prop-1-ynyl-1,3-dihydropyrimidine-2,4-dione, 5-(3-hydroxyprop-1-ynyl)-1,3-dihydropyrimidine-2,4-dione, 6-amino-5-prop-1-ynyl-3-dihydropyrimidine-2-one, 6-amino-5-(3-hydroxyprop-1-yny)-1,3-dihydropyrimidine-2-one, 6-amino-5-(3-aminoprop-1-yny)-1,3-dihydropyrimidine-2-one, 5-[4-amino-3-(3-methoxyprop-1-ynyl)pyrazol[3,4-d] pyrimidinyl]-2-(hydroxymethyl)oxolan-3-ol, 6-amino-1-[4-hydroxy-5-(hydroxymethyl)oxolan-2-yl]-3-(3-methoxyprop-1-ynyl)-5-hydropyrazolo[3,4-d]pyrimidin-4-one, 4-(4,6-Diamino-1H-pyrazolo[3,4-d]pyrimidin-3-yl)-but-3-yn-1-ol (Super A®), 6-Amino-3-(4-hydroxy-but-1-ynyl)-1,5-dihydro-pyrazolo[3,4-d]pyrimidin-4-one, 5-(4-hydroxy-but-1-ynyl)-1H-pyrimidine-2,4-dione (Super T®), 3-iodo-1H-pyrazolo[3,4-d]pyrimidine-4,6-diamine, 3-bromo-1H-pyrazolo[3,4-d]pyrimidine-4,6-diamine, 3-chloro-1H-pyrazolo[3,4-d]pyrimidine-4,6-diamine, 3-Iodo-1H-pyrazolo[3,4-d]pyrimidin-4-ylamine, 3-Bromo-1H-pyrazolo[3,4-d]pyrimidin-4-ylamine and 3-chloro-1H-pyrazolo[3,4-d]pyrimidin-4-ylamine. Examples of universal bases can be found in co-owned U.S. Application US2013/0261014 incorporated by reference herein.

The terms "fluorescent label" or "fluorophore" refer to compounds with a fluorescent emission maximum between about 400 and about 900 nm. These compounds include, with their emission maxima in nm in brackets, Cy2™ (506), GFP (Red Shifted) (507), YO-PRO™-1 (509), YOYO™-1 (509), Calcein (517), FITC (518), FluorX™ (519), Alexa™ (520), Rhodamine 110 (520), 5-FAM (522), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO®-1 (533), JOE (548), BODIPY® 530/550 (550), Dil (565), BODIPY® 558/568 (568), BODIPY® 564/570 (570), Cy3™ (570), Alexa™546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red® (615), Nile Red (628), YO-PRO™-3 (631), YOYO®-3 (631), R-phycocyanin (642), C-Phycocyanin (648), TO-PRO™-3 (660), TOT®-3 (660), DiD DilC(5) (665), Cy5™ (670), Thiadicarbocyanine (671), and Cy5.5 (694). Additional fluorophores are disclosed in PCT Patent Publication No. WO 03/023357 and U.S. Pat. No. 7,671, 218. Examples of these and other suitable dye classes can be found in Haugland et al., Handbook of Fluorescent Probes and Research Chemicals, Sixth Ed., Molecular Probes, Eugene, Oreg. (1996); U.S. Pat. Nos. 3,194,805; 3,128,179; 5,187,288; 5,188,934; 5,227,487, 5,248,782; 5,304,645; 5,433,896; 5,442,045; 5,556,959; 5,583,236; 5,808,044; 5,852,191; 5,986,086; 6,020,481; 6,162,931; 6,180,295; and 6,221,604; EP Patent No. 1408366; Still other dyes are provided via online sites such as zeiss.com. Phosphonate dyes are disclosed in co-owned U.S. Pat. Nos. 7,671,218, 7,767,834 and 8,163,910.

There is extensive guidance in the art for selecting quencher and fluorophore pairs and their attachment to oligonucleotides (Haugland, 1996; U.S. Pat. Nos. 3,996,345, 4,351,760 and 8,410,255 and the like).

Preferred quenchers are described in co-owned U.S. Pat. Nos. 6,727,356 and 7,662,942.

In the description herein, the abbreviations M, FL, Q, CPG, and ODN refer to "minor groove binder," "fluorescent label" or "fluorophore," "quencher," "controlled pore glass" (as an example of a solid support), and "oligonucleotide" moieties or molecules, respectively, and in a manner which is apparent from context. The terms "probe" and "conjugate" are used interchangeably and preferably refer to an oligonucleotide having an attached minor groove binder, fluorophore, and quencher.

The terms "oligonucleotide," "nucleic acid," and "polynucleotide" are used interchangeably herein. These terms refer to a compound comprising nucleic acid, nucleotide, or its polymer in either single- or double-stranded form, e.g., DNA, RNA, analogs of natural nucleotides, and hybrids thereof. The terms encompass polymers containing modified or non-naturally-occurring nucleotides, or to any other type of polymer capable of stable base-pairing to DNA or RNA including, but not limited to, peptide nucleic acids as described in Nielsen et al., Science, 254:1497-1500 (1991), bicyclo DNA oligomers as described in Bolli et al., Nucleic Acids Res., 24:4660-4667 (1996), and related structures. Unless otherwise limited, the terms encompass known analogs of natural nucleotides that hybridize to nucleic acids in a manner similar to naturally-occurring nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs) and any combination thereof. A "subsequence" or "segment" refers to a sequence of nucleotides that comprise a part of a longer sequence of nucleotides.

The term "internal control" refers to a control amplification reaction that monitors false negative amplification of targets due to failure of one or more reagents, failure of amplification due to thermal cycling, inhibition of amplification, or failure of reporting the reaction. The use of Bacteriophage MS2 (Dreier et al., J Clin Microbial. 43(9): 4551-7(2005)) and purified *Bacillus atrophaeus* subsp. *globigii* spores as internal controls (Picard et al. (2009)) have been reported. Practical considerations in design of competitive and non-competitive internal controls have also been reported in the field (Hoorfar et al. (2004)).

The practice of the methods described herein will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); and Eckstein (ed.), OLIGONUCLEOTIDES AND ANALOGUES: A PRACTICAL APPROACH, IRL Press (1991).

III. Description

Preferred embodiments herein are directed to primers and probes for use in methods for specific amplifying and/or detecting NDM1, KPC, IMP, VIM and OXA gene nucleic acids. Primers and probes of the invention are suitable to be used in the methods of the invention to detect NDM1, KPC, IMP, VIM and OXA sequences either simultaneously in a single reaction or in separate reactions. Typically, the amplification methods are performed on NDM1, KPC, IMP, VIM and OXA nucleic acids. One such amplification method is the polymerase chain reaction (PCR) (see, e.g., U.S. Pat. Nos. 4,683,195 and 4,965,188; Mullis et al. (1986)).

Amplification procedures are those in which many copies of a target nucleic acid sequence are generated, usually in an exponential fashion, by sequential polymerization and/or ligation reactions. In addition to the more traditional amplification reactions discussed below, the present method is useful in amplifications involving three-way junctures (see, e.g., WO 99/37085), signal amplification (see, e.g., Capaldi, et al. (2000)), T7 polymerases, reverse transcriptase, RNase H, RT-PCR, Rolling Circles, cleavase and the like. Isothermal amplification methods have been discussed (Niemz, A. (2011)). The term "oligonucleotide primers adjacent to a probe region" refers to when 0 or one or more bases separate the primer and probe. The term "overlapping with said probe region" is defined as disclosed in U.S. Pat. No. 7,319,022. The term "Ct" refers to the fractional PCR cycle number at which the reporter fluorescence is greater than the threshold.

Accordingly, in a first aspect, the invention provides methods for detecting NDM1, KPC, IMP, VIM and OXA nucleic acids in a sample, comprising:

(a) contacting a sample suspected of containing the NDM1, KPC, IMP, VIM or OXA nucleic acids with at least one flap primer having the formula:

$$5'\text{-}[X]n\text{-}Y\text{-}3' \qquad (I),$$

wherein X represents the 5' portion of the flap primer that is non-complementary to the NDM1, KPC, IMP, VIM or OXA nucleic acids, Y represents the 3' portion of the flap primer that is complementary to the NDM1, KPC, IMP, VIM or OXA nucleic acids, wherein X is about 3-30 nucleotides in length and n=0 or 1;

(b) incubating the mixture of step (a) under conditions sufficient to amplify the NDM1, KPC, IMP, VIM or OXA nucleic acids, thereby generating amplified NDM1, KPC, IMP, VIM or OXA nucleic acids; and (c) detecting the amplified NDM1, KPC, IMP, VIM or OXA nucleic acids.

In some embodiments the at least one flap primer comprises more than one primer sequence. In some embodiments a fluorescence-generating probe is used to detect the amplified NDM1, KPC, IMP, VIM and OXA nucleic acids. In some embodiment the fluorescence-generating probe comprises more than one sequence. The more than one probe sequence may be labeled with different fluorescence-generating dyes. The probe may contain a minor groove binder.

In some embodiments the more than one fluorescence-generating probe may be labeled with the same fluorescence emitting dye. In a preferred embodiment the more than one probe may be labeled with more than one different fluorescence emitting dyes.

In carrying out the preferred methods, the reaction mixture typically comprises at least two flap primers: a forward flap primer and a reverse flap primer. The forward flap primer and the reverse flap primer can be, but need not be, of equal lengths.

In one embodiment, the 5' sequence portion of the flap primer that is non-complementary to the NDM1, KPC, IMP, VIM or OXA nucleic acid (X) is about 1-15 nucleotides in length, usually about 4-14 or about 4-13 nucleotides in length, and more usually about 4-12 nucleotides in length. The 5' sequence portion of the flap primer that is non-complementary to the NDM1, KPC, IMP, VIM or OXA nucleic acid (X) can be 1, 2, 3, 4, 5, 6, 7, 8, 9, 10, 11, 12, 13, 14, or 15 nucleotides in length. In preferred embodiments, the primer is about 30 nucleotides in length overall. If the complementary sequence is less than 30 nucleotides, then a flap may be used to produce a 30-mer primer.

In certain instances, the 3' sequence portion of the flap primer that is complementary to the NDM1, KPC, IMP, VIM or OXA nucleic acid (Y) comprises a greater number of nucleotides than the 5' sequence portion of the flap primer that is non-complementary to the NDM1, KPC, IMP, VIM or OXA nucleic acid (X). For example, the 3' sequence portion of the flap primer that is complementary to the NDM1, KPC, IMP, VIM or OXA nucleic acid (Y) can comprise about 55%, 60%, 65%, 70%, 75%, 80%, 85%, or 90% of the total length of a flap primer.

In certain other instances, the 5' sequence portion of the flap primer that is non-complementary to the NDM1, KPC, IMP, VIM or OXA nucleic acid (X) comprises about an equal number of nucleotides as the 3' sequence portion of the flap primer that is complementary to the NDM1, KPC, IMP, VIM or OXA nucleic acid (Y). For example, the X and Y portions each can be about 4-30, 6-25, 8-20, or 10-15 nucleotides in length, usually about 10-14 or 11-13 nucleotides in length, and more usually about 12 nucleotides in length. The X and Y portions each can be 4, 5, 6, 7, 8, 9, 10, 11, 12, 13, 14, 15, 16, 17, 18, 19, 20, 21, 22, 23, 24, 25, 26, 27, 28, 29, or 30 nucleotides in length.

In another embodiment, the 5' sequence portion of the flap primer that is non-complementary to the NDM1, KPC, IMP, VIM or OXA nucleic acid (X) comprises at least about 60%, 65%, 70%, 75%, 80%, 90%, or 95% adenine or thymine nucleotide bases, or modified bases thereof.

In some embodiments, the 5' sequence portion of the flap primer that is non-complementary to the NDM1, KPC, IMP, VIM and OXA nucleic acids (X) comprises the following sequence or a portions of it: aataaatcataa (SEQ ID NO: 28). Shorter versions such as SEQ ID NOs: 29-32 can also be used. The non-complementary flap sequence of SEQ ID NO: 28 is found, for example, in SEQ ID NOs: 3, 18 or 19, including an additional oligonucleotide sequence. In other embodiments of the flap primers, the Y portion of the first flap primer comprises sequences substantially complementary to at least a portion of the KPC nucleic acid namely the primers of SEQ ID NOs: 2 or 3; IMP nucleic acid namely the primers of SEQ ID NOs: 8, 9, 10, 11 or 12; VIM nucleic acid namely the primers of SEQ ID NOs: 14, 15 or 16; NDM nucleic acid namely the primers of SEQ ID NOs: 18 or 19 and OXA nucleic acid namely the primers of SEQ ID NOs: 21 or 22. Sequences are shown below in Table 1. "Substantially complementary to at least a portion of" means that the sequence is complementary enough to the NDM1, KPC, IMP, VIM or OXA sequence that it will hybridize and result in amplification of the NDM1, KPC, IMP, VIM or OXA sequence. "Substantial identity" more specifically means about 85% complementary.

TABLE 1

| SEQ ID NO | Name | Sequence 5'-3' |
|---|---|---|
| 1 | KPC-FAM-1 | $R_{a1}$-G*CAGGTTCCGGTTTTG-$R_{b1}$-MGB |
| 2 | KPC-L1 | aataaatcatGTCATTTGCCGTGCCATAC |
| 3 | KPC-E1 | aataaatcataaGCAGACTGGGCAGTCGG |
| 4 | IMP-AP593-4 | $R_{a2}$-G*GI*CACACTCCAGATAAC-$R_{b1}$-MGB |
| 5 | IMP-AP593-5 | $R_{a2}$-G*GI*CACACTCAAGATAAC-$R_{b1}$-MGB |
| 6 | IMP-AP593-15 | $R_{a2}$-G*CTGA*A*TTAA*CI*AATGAGC-$R_{b1}$-MGB |
| 7 | IMP-AP593-16 | $R_{a2}$-G*CTGA*A*TTAA*CI*AATGAAC-$R_{b1}$-MGB |
| 8 | IMP-L1 | aataaatcatGGAATA*GAGTGGCTTAATTCTC |
| 9 | IMP-L2 | aataaatcatGGAATA*GGGTGGCTTAATTCTC |

TABLE 1-continued

| SEQ ID NO | Name | Sequence 5'-3' |
|---|---|---|
| 10 | IMP-L3 | aataaatcatGGAATA*GAATGGCTTAACTCTC |
| 11 | IMP-E7 | aataaatAGGCAACCAAACCACTACGTTATCT |
| 12 | IMP-E8 | aataaatAGGCAGCCAAACTACTAGGTTATCT |
| 13 | VIM-AP593-7 | $R_{a2}$-G*TGCGCTTCGGTCC-$R_{b1}$-MGB |
| 14 | VIM-L4 | aataaCGCATTCTCTAGAAGGACTCTCATC |
| 15 | VIM-L6 | aataaCGCACTCTCTAAAAGCGCTCTCCTC |
| 16 | VIM-E6 | aataaatcaCGAATGCGCAGCACCI*GGATAGA |
| 17 | NDM-AP593-2 | $R_{a2}$-G*ACATGCCGGGTTTC-$R_{b1}$-MGB |
| 18 | NDM-L2 | aataaatcataaGTCTGGCAGCACACTTCCTA |
| 19 | NDM-E2 | aataaatcataaCGCCATCCCTGACGATCAAAC |
| 20 | OXA-AP662-7 | $R_{a1}$-G*TGTTTTTGGTGGCATCG-$R_{b1}$MGB |
| 21 | OXA-L1 | aataaatcaATGCGTGTATTAGCCTTATCGGC |
| 22 | OXA-E1 | aataaatcatTCTTGCCATTCCTTTGCTACCG |
| 23 | E6132-L | CTGCACGGACCAGTTACTTTACG |
| 24 | E6132-E | CTCATTTTTTCTACCGGAGATCTTGT |
| 25 | E6132-AP525-TM3 | $R_{a4}$-G*ACCACGTACCGCATTG-$R_{b1}$-MGB (MGB phosphoramidite) |
| 26 | OXA-Qzr705-1 | $R_{a5}$-G*GTGGCATCGATTATC-$R_{b2}$-MGB |
| 27 | OXA-AP662-7 | $R_{a6}$-G*TGTTTTTGGTGGCATCG-$R_{b3}$ |
| 28 | Flap | aataaatcataa |
| 29 | Flap | aataaatcat |
| 30 | Flap | aataaatca |
| 31 | Flap | aataaat |
| 32 | Flap | aataa |

Where G* = Super G;
A* = Super A,
I* = 3-aminobutynyl-1H-pyrazolo[3,4-d]pyrimidin-4(5H)-one;
$R_{a1}$ = FAM;
$R_{a2}$ = AP593;
$R_{a3}$ = AP662;
$R_{a4}$ = AP525;
$R_{a5}$ = Quasar 705 (Biosearch Technology, Petaluma, CA);
$R_{a6}$ = MGB-$R_{a3}$;
$R_{b1}$ = Eclipse® Dark Quencher-MGB;
$R_{b2}$ = Quencher575-MGB and $R_{b3}$ = Eclipse Dark Quencher.
Quencher575 = (E)-4-((4-((2-chloro-4-nitrophenyl)diazenyl)-2,5-dimethoxyphenyl)(ethyl)amino)butanoic acid.
AP = AquaPhlour Dye-IW with emission wavelength (IW) noted.
Lower case represents flap sequences.

In additional embodiments, primers and probes are designed to target portions of two different KPC sequences at different locations, namely, location 2, at 945 to 997, and location 3, at 565 to 627 (Yigit et al.), as shown below in Table 2.

TABLE 2

| | | Location 2 |
|---|---|---|
| 34 | KPC-E2 | AATAAATCATAAACAGCGAGGCCGTCATC |
| 35 | KPC-L3 | AATAAATCATAACCCAATCCCTCGAGCG |
| 36 | KPC-L4 | AATAAATCATAACCCAATCCCTCGAGCGC |
| 37 | KPC-F2 | FAM-G*AGTCTAGCCGCAGCG-EDQ-MGB |
| 38 | KPC-F3 | FAM-G*TCTAGCCGCAGCGG-EDQ-MGB |
| | | Location 3 |
| 39 | KPC-L5 | AATAAATCATAACGGGCTGACGGCCTTCATG |
| 40 | KPC-E3 | AATAAATCATAAAGCTCCCAGCGGTCCAGA |
| 41 | KPC-F4 | FAM-G*CGATACCACGTTCCG-EDQ-MGB |
| 42 | KPC-F5 | FAM-G*TGGTATCGCCGATAGA-EDQ-MGB |
| 43 | KPC-F6 | MGB-FAM-G*GCGATACCACGTTCCG-EDQ |

Where G* = Super G;
EDQ = Eclipse® Dark Quencher;
Underline represents flap sequences.

In further embodiments, primers and probes are designed to target portions of additional different IMP sequences at different locations, namely, location 2, at 945 to 997, and location 3, at 565 to 627 (Yigit et al.), as shown below in Table 3.

TABLE 3

| SEQ ID NO: | Name | Sequence 5'-3' |
|---|---|---|
| | | Location 2 |
| 44 | IMP-L5 | GTTTATGTTCATACI*TCGTTTGAA GAI*GTTAA |
| 45 | IMP-L6 | GTTTATGTTCATACI*TCGITCGAA GAI*GTTAA |
| 46 | IMP-E5 | AATAAATACAAGAACCACCAAI*CC I*TGTTTAG |
| 47 | IMP-E6 | AATAAATACAAGAACCACTAAI*CC I*TGTTTAG |
| 48 | IMP-AP593-2 | AP593-G*A*A*CAACI*CCCCAI* CC-EDQ-MGB |
| 49 | IMP-AP593-7 | MGB-AP593-G*GI*CACA*CTCA* AGA*T-EDQ |
| | | Location 3 |
| 50 | IMP-L7 | AAI*AAI*AAI*ATTGAAGTTTTTT ATCCI*GGCCC |
| 51 | IMP-L8 | TATTGGCTAGTTAAI*AAI*AAI*A TTGA*AI*TTTT |
| 52 | IMP-E7 | AATAAATAGGCAACCAAACCACTAC GTTATCT |
| 53 | IMP-E8 | AATAAATAGGCAGCCAAACTACTAG GTTATCT |

TABLE 3-continued

| SEQ ID NO: | Name | Sequence 5'-3' |
|---|---|---|
| 54 | IMP-AP593-3 | AP593-G*GI*CA*CA*CTCA*AGA T-EDQ-MGB |
| 55 | IMP-AP593-7 | MGB-AP593-G*GI*CACA*CTCA* AGA*T-MGB |

Where G* = Super G;
A* = Super A, I* = 3-aminobutynyl-1H-pyrazolo[3,4-d]pyrimidin-4(5H)-one;
EDQ = Eclipse® Dark Quencher.
Underline represents flap sequences.

In further embodiments, primers and probes are designed to target portions of additional different VIM sequences at different locations, namely, location 2, at 172 to 541, and location 3, at 562 to 636 (Papagiannitsis et al.), as shown below in Table 4.

TABLE 4

| SEQ ID NO: | Name | Sequence 5'-3' |
|---|---|---|
| | | Location 2 |
| 56 | VIM-L3 | AATAAATCATAAGGCA*CTTC TCGCGGAGATTG |
| 57 | VIM-E2 | AATAAATCATAAGACGCGGTC GTCATGAAAG |
| 58 | VIM-E3 | AATAAATCATAAGACGCGI*T CGTCATGI*AAG |
| 59 | VIM-E4 | AATAAATCATACGTGGAGACT GCI*CGCGTTAC |
| 60 | VIM-AP593-2 | AP593-G*AAGCAAATTGGAC TTCC-EDQ-MGB |
| 61 | VIM-AP593-5 | MGB-AP593-G*AAGCAAATT GGA*CTTCC-EDQ |
| | | Location 3 |
| 62 | VIM-L4 | AATAACGCATTCTCTAGAAGG ACTCTCATC |
| 63 | VIM-E5 | AATAAATCATATGCGCAGCAC CI*GGATAGAAG |
| 64 | VIM-AP593-3 | AP593-G*CGCTTCGGTCCAG TAG-EDQ-MGB |
| 65 | VIM-AP593-6 | MGB-AP593-G*CGCTTCGGT CCAGTA*G-EDQ |

Where G* = Super G;
A* = Super A, I* = 3-aminobutynyl-1H-pyrazolo[3,4-d]pyrimidin-4(5H)-one;
EDQ = Eclipse® Dark Quencher.
Underline represents flap sequences.

In further embodiments, primers and probes are designed to target portions of additional different NDM1 sequences at two different locations, namely, location 2, at 213 to 292, and location 3, at 453 to 573 (Yong et al.), as shown below in Table 5.

TABLE 5

| SEQ ID NO: | Name | Sequence 5'-3' |
|---|---|---|
| Location 2 | | |
| 66 | NDM-L2 | AATAAATCATAAGTCTGGCAGCACACTTCCTA |
| 67 | NDM-E2 | AATAAATCATAACGCCATCCCTGACGATCAAAC |
| 68 | NDM-AP593-2 | AP593-G*ACATGCCGGGTTTC-EDQ-MGB |
| Location 3 | | |
| 69 | NDM-L3 | AATAAATCATAATACCGCCTGGACCI*ATGAC |
| 70 | NDM-E3 | AATAAATCATAAACCGGCAGGTTGATCTCCT |
| 71 | NDM-AP593-3 | AP593-G*CCCAGATCCTCAACTG-EDQ-MGB |

Where G* = Super G, I* = 3-aminobutynyl-1H-pyrazolo[3,4-d]pyrimidin-4(5H)-one;
EDQ = Eclipse® Dark Quencher.
Underline represents flap sequences.

In further embodiments, primers and probes are designed to target portions of additional different OXA-48 sequences at different locations, namely, location 2, at 179 to 299, and location 3, at 599 to 631 (Poirel et al.), as shown below in Table 6. These primers and probes are also specific for OXA-181 (Potron et al.).

TABLE 6

| SEQ ID NO: | Name | Sequence 5'-3' |
|---|---|---|
| Location 2 | | |
| 72 | OXA-E2 | AATAAATCATAAAAACGGGCGAACCAAGCA |
| 73 | OXA-L2 | AATAAATCATAACGCGTCTGTCCATCCCACTT |
| 74 | OXA-AP662-2 | AP662-G*CTATTGGGAAT*T*T*T*AAAG-EDQ-MGB |
| Location 3 | | |
| 75 | OXA-L3 | AATAAATCATACCGAAGCCAATGGTGACTATA |
| 76 | OXA-E3 | AATAAATCAACCI*ACCCACCAGCCAATCTTAG |
| 77 | OXA-AP662-3 | AP662-G*GCTAAAACI*GGATACTC-EDQ-MGB |
| 78 | OXA-AP662-6 | MGB-AP662-G*CTAAAACI*GGATA*CTCG-EDQ |

Where G* = Super G, I* = 3-aminobutynyl-1H-pyrazolo[3,4-d]pyrimidin-4(5H)-one;
T* is Super T, or 5-(4-hydroxy-but-1-ynyl)-1H-pyrimidine-2,4-dione;
EDQ = Eclipse® Dark Quencher.
Underline represents flap sequences.

The sample is typically obtained from a mammal suspected of having a bacterial infection with potential NDM1, KPC, IMP, VIM or OXA antibiotic resistant involvement. Preferably, the mammal is a human. Examples of samples suitable for use in the methods of the invention include, but are not limited to a rectal swab.

Generally, the methods produce a detectable signal when the probe hybridizes to the amplified target (U.S. Pat. Nos. 7,381,818 and 7,759,126). In addition this method allows the post-amplification melting curve analysis. Alternatively, the fluorescent probe is cleaved by using a nucleic acid polymerase having 5'-3' nuclease activity to yield a fluorescent signal (U.S. Pat. No. 5,538,848). Further, the methods are particularly suited to continuous monitoring of a detectable signal ("real-time detection"). In certain embodiments, simultaneous amplification is detected using a fluorescence-generating probe, for example, a hybridization-based fluorescent probe or a nucleic acid binding fluorescent compound.

Amplified NDM1, KPC, IMP, VIM or OXA nucleic acid can be detected using any of the methods of detection known in the art. For example, detection can be carried out after completion of an amplification reaction (e.g., using ethidium bromide in an agarose gel) or simultaneously during an amplification reaction ("real-time detection") (McPherson et al., 2000; and Wittwer et al. (2004)). Preferably, the amplified NDM1, KPC, IMP, VIM or OXA nucleic acid is detected by hybridization to a probe that specifically binds to the amplified NDM1, KPC, IMP, VIM or OXA nucleic acids. In certain instances, the amplified NDM1, KPC, IMP, VIM or OXA nucleic acids is detected using one or more fluorescence-generating probes. Fluorescence-generating probes include probes that are cleaved to release fluorescence (e.g. U.S. Pat. Nos. 5,538,848, 7,790,385 etc.), nucleic acid binding compounds (e.g., U.S. Pat. No. 5,994,056; Bengtsson et al., 2003), hybridization-based probes (e.g., U.S. Pat. Nos. 5,925,517, 7,205,105, 7,381,818, etc.), and the like. In certain embodiments, the NDM1, KPC, IMP, VIM or OXA nucleic acid is detected with one or more nucleic acid binding fluorescent compounds (e.g., SYBR® Green 1 (Molecular Probes; Eugene, Oreg.), or BOXTOX, BEBO (TATAA Biocenter; Gotenborg, Sweeden), or the like).

In one embodiment, the NDM1, KPC, IMP, VIM or OXA nucleic acid is detected using a fluorescence-generating probe, disclosed in Table 1, that hybridizes to the NDM1, KPC, IMP, VIM or OXA nucleic acids and one or more nucleotide bases of at least one flap primer sequence (typically, the complementary portion, Y). For example, the fluorescence-generating probe can hybridize to the NDM1, KPC, IMP, VIM or OXA nucleic acid and to one or more nucleotide bases of the forward flap primer sequence, one or more nucleotide bases of the reverse flap primer sequence, or simultaneously to one or more nucleotide bases of both the forward and the reverse flap primer sequences. The fluorescence-generating probe can optionally hybridize to the NDM1, KPC, IMP, VIM or OXA nucleic acid and to 1, 2, 3, 4, 5, 6, 7, 8, 9, or 10 nucleotide bases of at least one flap primer sequence, particularly the complementary portion (Y) of a flap primer.

In preferred embodiment, the fluorescence-generating probes of the invention comprise at least one of the following sequences:

$R_{a1}$-G*CAGGTTCCGGTTTTG-$R_{b1}$ (SEQ ID NO: 1)

$R_{a2}$-G*GI*CACACTCCAGATAAC-$R_{b1}$ (SEQ ID NO: 4)

$R_{a2}$-G*GI*CACACTCAAGATAAC-$R_{b1}$ (SEQ ID NO: 5)

-continued

R$_{a2}$-G*CTGA*A*TTAA*CI*AATGAGC-R$_{b1}$ (SEQ ID NO: 6)

R$_{a2}$-G*CTGA*A*TTAA*CI*AATGAAC-R$_{b1}$ (SEQ ID NO: 7)

R$_{a2}$-G*TGCGCTTCGGTCC-R$_{b1}$ (SEQ ID NO: 13)

R$_{a2}$-G*ACATGCCGGGTTTC-R$_{b1}$ (SEQ ID NO: 17)

R$_{a3}$-G*TGTTTTTGGTGGCATCG-R$_{b1}$ (SEQ ID NO: 20)

R$_{a5}$-G*GTGGCATCGATTATC-R$_{b2}$ (SEQ ID NO: 26)

R$_{a6}$-G*TGTTTTTGGTGGCATCG-R$_{b3}$ (SEQ ID NO: 27)

wherein G*=Super G; A*=Super A, I*=3-aminobutynyl-1H-pyrazolo[3,4-d]pyrimidin-4(5H)-one; R$_{a1}$=FAM; R$_{a2}$=AP593; R$_{a3}$=AP662; R$_{a4}$=AP525; R$_{a5}$=Quasar 705 (Biosearch Technology, Petaluma, Calif.); R$_{a6}$=MGB-R$_{a3}$; R$_{b1}$=Eclipse® Dark Quencher-MGB; R$_{b2}$=Quencher575-MGB and R$_{b3}$=Eclipse® Dark Quencher. Quencher575= (E)-4-((4-((2-chloro-4-nitrophenyl)diazenyl)-2,5-dimethoxyphenyl)(ethyl)amino)butanoic acid. AP=AquaPhlour Dye-IW with emission wavelength (IW) noted.

In a preferred embodiment the fluorophores are FAM, AquaPhluor® 525 with an excitation wavelength of 525 nm, AquaPhluor 593 with an excitation wavelength of 593 nm, AquaPhluor 662 aELITechgroup Molecular Diagnostics, Bothell, Wash.) with an excitation wavelength of 662 nm and Quazar 705 (Biosearch Technologies).

In additional preferred embodiments, the fluorescence generating probes of the invention comprise at least one of the following sequences: SEQ ID NO: 1, 4, 5, 6, 7, 13, 17, 20, 26, 37, 38, 41, 42, 43, 48, 49, 54, 55, 60, 61, 64, 65, 68, 71, 74, 77, 78, 79, 80, 81, 82, or 83, as shown above in Tables 1-6.

The primers can incorporate additional features which allow for the detection or immobilization of the primer but do not alter the basic property of the primer, e.g., to act as a point of initiation of nucleic acid synthesis. In some instances, the primers contain one or more non-natural bases or modified bases in either or both the complementary and non-complementary sequence regions of the primer.

In certain instances, amplification is carried out using a polymerase. The polymerase can, but need not, have 5' nuclease activity. In certain other instances, primer extension is carried out using a reverse transcriptase and amplification is carried out using a polymerase.

In another embodiment, the primer sequences overlap, wherein the stability of the overlapping sequence duplex is less than that of the stability of the individual primer target duplexes.

In preferred embodiments, the primers of the invention, which include both forward and reverse flap primers, comprise at least one of the following sequences: SEQ ID NO: 2, 3, 8, 9, 10, 11, 12 14, 15, 16, 18, 19, 21, 22, 34, 35, 36, 39, 40, 44, 45, 46, 47, 50, 51, 52, 53, 56, 57, 58, 59, 62, 63, 66, 67, 69, 70, 72, 73, 75, or 76, as shown above in Tables 1-6.

In another aspect, the invention provides methods for simultaneously detecting nucleic acids from NDM1, KPC, IMP, VIM and OXA in a sample, comprising:

(a) contacting a sample suspected of containing the NDM1, KPC, IMP, VIM or OXA nucleic acids with:
(i) at least one forward flap primer comprising at least one of the following sequences:

aataaatcataaGCAGACTGGGCAGTCGG, (SEQ ID NO: 3)

aataaatAGGCAACCAAACCACTACGTTATCT, (SEQ ID NO: 11)

aataaatAGGCAGCCAAACTACTAGGTTATCT, (SEQ ID NO: 12)

aataaatcaCGAATGCGCAGCACCI*GGATAGA, (SEQ ID NO: 16)

aataaatcataaCGCCATCCCTGACGATCAAAC, (SEQ ID NO: 19)
and aataaatcatTCTTGCCATTCCTTTGCTACCG, (SEQ ID NO: 22)

wherein the lowercase nucleotide sequence is non-complementary to sequences of the NDM1, KPC, IMP, VIM or OXA nucleic acids; and
(ii) at least one reverse flap primer comprising at least one of the following sequences:

aataaatcatGTCATTTGCCGTGCCATAC, (SEQ ID NO: 2)

aataaatcatGGAATA*GAGTGGCTTAATTCTC, (SEQ ID NO: 8)

aataaatcatGGAATA*GGGTGGCTTAATTCTC, (SEQ ID NO: 9)

aataaatcatGGAATA*GAATGGCTTAACTCTC, (SEQ ID NO: 10)

aataaCGCATTCTCTAGAAGGACTCTCATC, (SEQ ID NO: 14)

aataaCGCACTCTCTAAAAGCGCTCTCCTC, (SEQ ID NO: 15)

aataaatcataaGTCTGGCAGCACACTTCCTA, (SEQ ID NO: 18)
and aataaatcaATGCGTGTATTAGCCTTATCGGC, (SEQ ID NO: 21)

wherein the lowercase nucleotide sequence is non-complementary to sequences of the NDM1, KPC, IMP, VIM or OXA nucleic acids;
(b) incubating the reaction mixture of step (a) under conditions sufficient to amplify the NDM1, KPC, IMP, VIM or OXA nucleic acids, thereby generating amplified NDM1, KPC, IMP, VIM or OXA nucleic acids from bacteria containing the NDM1, KPC, IMP, VIM or OXA genes that carry antibiotic resistance; and
(c) detecting the amplified NDM1, KPC, IMP, VIM or OXA nucleic acids.

Some embodiments comprise primer ratios that allow asymmetric amplification of the NDM1, KPC, IMP, VIM or OXA nucleic acids.

The sample is typically obtained from a mammal suspected of having an infection of an organism that carries carbapenem-resistant Enterobacteriaceae, (CRE). Preferably, the mammal is a human. Typical sample suitable for use in the methods of the invention contain CRE containing organisms, preferably rectal swabs.

In some embodiments, continuous monitoring of a detectable signal ("real-time detection") is used to detect the signal. In certain embodiments, simultaneous amplification is detected using a fluorescence-generating probe, for example, a hybridization-based fluorescent probe, a probe with a cleaving-site or a nucleic acid binding fluorescent compound. In some embodiments, end-point fluorescent measurement using a dissociation curve analysis is used to detect the signal.

In yet another aspect, kits are provided for detecting NDM1, KPC, IMP, VIM or OXA nucleic acids in a sample, comprising:

at least one forward flap primer comprising at least one of the following sequences:

(SEQ ID NO: 3)
aataaatcataaGCAGACTGGGCAGTCGG, (SEQ ID NO: 11)
aataaatAGGCAACCAAACCACTACGTTATCT, (SEQ ID NO: 12)
aataaatAGGCAGCCAAACTACTAGGTTATCT, (SEQ ID NO: 16)
aataaatcaCGAATGCGCAGCACCI*GGATAGA, (SEQ ID NO: 19)
aataaatcataaCGCCATCCCTGACGATCAAAC,
and (SEQ ID NO: 22)
aataaatcatTCTTGCCATTCCTTTGCTACCG, wherein the underlined nucleotide sequence is non-complementary to sequences of the NDM1, KPC, IMP, VIM or OXA nucleic acids; and at least one reverse flap primer comprising at least one of the following sequences:

(SEQ ID NO: 2)
aataaatcatGTCATTTGCCGTGCCATAC, (SEQ ID NO: 8)
aataaatcatGGAATA*GAGTGGCTTAATTCTC, (SEQ ID NO: 9)
aataaatcatGGAATA*GGGTGGCTTAATTCTC, (SEQ ID NO: 10)
aataaatcatGGAATA*GAATGGCTTAACTCTC, (SEQ ID NO: 14)
aataaCGCATTCTCTAGAAGGACTCTCATC, (SEQ ID NO: 15)
aataaCGCACTCTCTAAAAGCGCTCTCCTC, (SEQ ID NO: 18)
'aataaatcataaGTCTGGCAGCACACTTCCTA,
and (SEQ ID NO: 21)
aataaatcaATGCGTGTATTAGCCTTATCGGC, wherein the underlined nucleotide sequence is non-complementary to sequences of the NDM1, KPC, IMP, VIM or OXA nucleic acids.

In certain instances, the kits further comprise a fluorescence-generating probe such as a hybridization-based fluorescent probe for detecting NDM1, KPC, IMP, VIM or OXA including a nucleic acid binding fluorescent compound. In a preferred embodiment, the fluorescence-generating probes comprise at least one of the following sequences:

(SEQ ID NO: 1)
$R_{a1}$-G*CAGGTTCCGGTTTTG-$R_{b1}$, (SEQ ID NO: 4)
$R_{a2}$-G*GI*CACACTCCAGATAAC-$R_{b1}$, (SEQ ID NO: 5)
$R_{a2}$-G*GI*CACACTCAAGATAAC-$R_{b1}$, (SEQ ID NO: 6)
$R_{a2}$-G*CTGA*A*TTAA*CI*AATGAGC-$R_{b1}$, (SEQ ID NO: 7)
$R_{a2}$-G*CTGA*A*TTAA*CI*AATGAAC-$R_{b1}$, (SEQ ID NO: 13)
$R_{a2}$-G*TGCGCTTCGGTCC-$R_{b1}$, (SEQ ID NO: 17)
$R_{a2}$-G*ACATGCCGGGTTTC-$R_{b1}$, (SEQ ID NO: 20)
$R_{a3}$-G*TGTTTTTGGTGGCATCG-$R_{b1}$, (SEQ ID NO: 26)
$R_{a5}$-G*GTGGCATCGATTATC-$R_{b2}$,
and (SEQ ID NO: 27)
$R_{a6}$-G*TGTTTTTGGTGGCATCG-$R_{b3}$, where G*=Super G; A*=Super A, I*=3-aminobutynyl-1H-pyrazolo[3,4-d]pyrimidin-4(5H)-one; $R_{a1}$=FAM; $R_{a2}$=AP593; $R_{a3}$=AP662; $R_{a4}$=AP525; $R_{a5}$=Quasar 705 (Biosearch Technology, Petaluma, Calif.); $R_{a6}$=MGB-$R_{a3}$; $R_{b1}$=Eclipse® Dark Quencher-MGB; $R_{b2}$=Quencher575-MGB and $R_{b3}$=Eclipse® Dark Quencher. Quencher575=(E)-4-((4-((2-chloro-4-nitrophenyl)diazenyl)-2,5-dimethoxyphenyl)(ethyl)amino) butanoic acid. AP=AquaPhlour Dye-IW with emission wavelength (IW) noted.

In a preferred embodiment the fluorophores are FAM, AquaPhluor® 525 with an excitation wavelength of 525 nm, AquaPhluor 593 with an excitation wavelength of 593 nm, AquaPhluor 662 ((ELITechgroup Molecular Diagnostics, Bothell, Wash.) with an excitation wavelength of 662 nm and Quazar 705.

In additional preferred embodiments, the fluorescence generating probes comprise at least one of the following sequences: SEQ ID NOS: 1, 4, 5, 6, 7, 13, 17, 20, 26, 27, 37, 38, 41, 42, 43, 48, 49, 54, 55, 60, 61, 64, 65, 68, 71, 74, 77, 78, 79, 80, 81, 82, or 83, as shown above in Tables 1-6.

In certain other instances, the kits further comprise a control nucleic acid that is suitable for use as an internal control. As a non-limiting example, the control nucleic acid can comprise a nucleic acid sequence containing at least a portion of SEQ ID NO:33. Preferably, the control nucleic acid comprises the following sequence:

(SEQ ID NO: 33)
5'-CTGCACGGACCAGTTACTTTACGGACCACGTACCGCATTGGTA
CAAGATCTCCGGTAGAAAAAATGAG-3'.

The kits of the invention can also comprise primers and probes directed against the control nucleic acid. As a non-limiting example, a control probe (e.g., a fluorescence-generating probe) and a set of control primers designed against the nucleic acid sequence SEQ ID NO:33 can be included in the kits. Preferably, the control probe and primers have the following sequences:

(i) Probe:
(SEQ ID NO: 25)
$R_a$-G*ACCACGTACCGCATTG-$R_b$, wherein G* is the guanine analogue 6-amino-1H-pyrazolo[3,4-d]pyrimidin-4(5H)-one, $R_a$ is independently selected from (M)$_a$-F1 and (M)$_a$-Q, $R_b$ is independently selected from (M)$_a$-F1 and (M)$_a$-Q, and M is a minor groove binder, a is 0 or 1, F1 is a fluorophore with emission wavelength between about 400 and 900 nm, and Q is a non-fluorescent quencher, with the proviso that the substitution of $R_a$ and $R_b$ allows quenching of fluorescence when the probe is unhybridized; and that the fluorophore has an emission wavelength different from that of the probe for detecting the nucleic acids from NDM1, KPC, IMP, VIM or OXA; and (ii) Primers:
(SEQ ID NO: 23)
CTGCACGGACCAGTTACTTTACG,
and (SEQ ID NO: 24)
CTCATTTTTTCTACCGGAGATCTTGT.

In a preferred embodiment F1 is AquaPhluor 525 with an excitation wavelength of 525 nm (ELITechgroup Molecular Diagnostics, Bothell, Wash.), "M" is a minor groove binder such as, for example DPI3, "G*" is PPG, and "Q" is the Eclipse® Dark Quencher.

In one aspect, the present invention provides target sequences suitable for specific detection and amplification of extended beta-lactamase resistant genes that involve NDM1, KPC, IMP, VIM or OXA.

The present method provides oligonucleotide primers ("overhang primers," "flap primers," or "adapter primers") which are most generally noted as 5'-(X)$_p$—Y-3' primers where p=0 or 1. X represents the sequence portion of the primer that is non-complementary to the NDM1, KPC, IMP, VIM or OXA nucleic acid, and Y represents the sequence portion of the primer that is complementary to the NDM1, KPC, IMP, VIM or OXA nucleic acid.

Accordingly, in one group of embodiments, the primer has the formula:

$$5'\text{-}(X)_p\text{—}Y\text{-}3' \quad (I),$$

wherein X represents the 5' sequence of the primer non-complementary to the NDM1, KPC, IMP, VIM or OXA nucleic acid, Y represents the complementary 3' sequence of the primer, p is 0 or 1, and X—Y represents the nucleic acid oligomer primer. In certain further embodiments, X is [A-B]$_m$ and Y is [A-B]$_n$, wherein A represents a sugar phosphate backbone, modified sugar phosphate backbone, locked nucleic acid backbone, or a variant thereof in any combination as used in nucleic acid preparation; B represents a nucleic acid base or a modified base of a base; and the subscripts m and n are integers of from about 4-30 or 5-25, 7-20, or 9-15, and more usually about 12. In certain embodiments, the values of the subscripts m and n are equal, for example, both m and n simultaneously can be an integer of from about 5-25, 7-20, or 9-15, and more usually about 12.

Primers and probes were designed to amplify and detect regions of the NDM1, KPC, IMP, VIM or OXA genes located on a transferable plasmid and more specifically NDM1, KPC, IMP, VIM or OXA nucleic acids that have substantial or absolute homology between members of respective groups. In some embodiments, the primers are flap primers comprising the following formula:

$$5'\text{-}(X)_p\text{—}Y\text{-}3' \quad (I),$$

wherein X represents the 5' portion of the flap primer that is non-complementary to the NDM1, KPC, IMP, VIM or OXA nucleic acid, Y represents the 3' portion of the flap primer that is complementary to the NDM1, KPC, IMP, VIM or OXA nucleic acid, and p is about 3-30, 5-25, 7-20, or 9-15.

The 5'-non-complementary sequences of the primers of this invention can be modified as taught in U.S. Patent Application 2007/0048758.

The primers and probes of the present invention are generally prepared using solid phase methods known to those of skill in the art. In general, the starting materials are commercially available, or can be prepared in a straightforward manner from commercially available starting materials using suitable functional group manipulations as described in, for example, March et al., ADVANCED ORGANIC CHEMISTRY—Reactions, Mechanisms and Structures, 4th ed., John Wiley & Sons, New York, N.Y. (1992).

In one embodiment, the primers and probes of the invention can comprise any naturally occurring nucleotides, non-naturally occurring nucleotides, or modified nucleotides known in the art (see, e.g., U.S. Patent Publication No. 20050118623; and U.S. Pat. No. 6,949,367, U.S. Patent Publication No. 20120244535).

The ability to design probes and primers in a predictable manner using an algorithm that can direct the use or incorporation of modified bases, minor groove binders, fluorophores, and/or quenchers based on their thermodynamic properties have been described in, e.g., U.S. Pat. No. 6,683,173. Accordingly, the use of any combination of normal bases, unsubstituted pyrazolo[3,4-d]pyrimidine bases (e.g., PPG and PPA), 3-substituted pyrazolo[3,4-d]pyrimidines, modified purines, modified pyrimidines, 5-substituted pyrimidines, universal bases, sugar modifications, backbone modifications, and/or minor groove binders to balance the Tm (e.g., within about 5-8° C.) of a hybridized product with a modified nucleic acid, reduce G-G self-association or to accommodate mismatches in primer or probe is contemplated by the present invention. Co-owned U.S. Patent Application 2012/0244535, incorporated by reference, provides additional explanation as to how to address primers and probes with as many as five mismatches in a primer.

Detailed descriptions of the chemistry used to synthesize oligonucleotides by the phosphoramidite method are provided in U.S. Pat. Nos. 4,458,066 and 4,415,732; Caruthers et al., Genetic Engineering, 4:1-17 (1982); and Users Manual Model 392 and 394 Polynucleotide Synthesizers, pages 6-1 through 6-22, Applied Biosystems, Part No. 901237 (1991). Labeled oligonucleotides can be synthesized by chemical synthesis, e.g., by a phosphoramidite method, a phosphite-triester method, and the like, (see, e.g., Gait, Oligonucleotide Synthesis, IRL Press (1990)). Labels can be introduced during enzymatic synthesis utilizing labeled nucleoside triphosphate monomers, or introduced during chemical synthesis using labeled non-nucleotide or nucleotide phosphoramidites, or may be introduced subsequent to synthesis.

A variety of linking groups and methods are known to those of skill in the art for attaching fluorophores, quenchers, and minor groove binders to the 5' or 3' termini of oligonucleotides. See, for example, Eckstein, (ed.), Oligonucleotides and Analogues: A Practical Approach, IRL Press, Oxford (1991); Zuckerman et al., Nuc. Acids Res., 15:5305-5321 (1987); Sharma et al., Nuc. Acids Res., 19:3019 (1991); Giusti et al., PCR Methods and Applications, 2:223-227 (1993), U.S. Pat. Nos. 4,757,141 and 4,739,044; Agrawal et al., Tetrahedron Letters, 31:1543-1546 (1990); Sproat et al., Nuc. Acids Res., 15:4837 (1987); Nelson et al., Nuc. Acids Res., 17:7187-7194 (1989); and the like. Still other commercially available linking groups can be used that can be attached to an oligonucleotide during synthesis and are available from, e.g., Clontech Laboratories (Palo Alto, Calif.). Other methodologies for attaching a fluorophore to an oligonucleotide portion involve the use of phosphoramidite chemistry at the conclusion of solid phase synthesis by way of dyes derivatized with a phosphoramidite moiety. See, e.g., U.S. Pat. Nos. 5,231,191; 4,997,928; 6,653,473; 6,790,945; and 6,972,339; and PCT Patent Publication No. WO 01/42505.

IV. Additional Amplification Reaction Components

Buffers

Buffers that may be employed are borate, phosphate, carbonate, barbital, Tris, etc., based buffers (see, e.g., U.S. Pat. No. 5,508,178). The pH of the reaction should be maintained in the range of from about 4.5 to about 9.5 (see, e.g., U.S. Pat. No. 5,508,178). The standard buffer used in amplification reactions is a Tris based buffer between 10 and 50 mM with a pH of around 8.3 to 8.8 (see, e.g., Innis et al., supra).

One of skill in the art will recognize that buffer conditions should be designed to allow for the function of all reactions of interest. Thus, buffer conditions can be designed to support the amplification reaction as well as any subsequent restriction enzyme reactions. A particular reaction buffer can be tested for its ability to support various reactions by testing the reactions both individually and in combination.

Salt Concentration

The concentration of salt present in the reaction can affect the ability of primers to anneal to the target nucleic acid (see, e.g., Innis et al., supra). Potassium chloride can be added up to a concentration of about 50 mM to the reaction mixture to promote primer annealing. Sodium chloride can also be added to promote primer annealing (see, e.g., Innis et al., supra).

Magnesium Ion Concentration

The concentration of magnesium ion in the reaction can affect amplification of the target nucleic acid sequence (see, e.g., Innis et al., supra). Primer annealing, strand denaturation, amplification specificity, primer-dimer formation, and enzyme activity are all examples of parameters that are affected by magnesium concentration (see, e.g., Innis et al., supra). Amplification reactions should contain about a 0.5 to 6.0 mM magnesium concentration excess over the concentration of dNTPs. The presence of magnesium chelators in the reaction can affect the optimal magnesium concentration. A series of amplification reactions can be carried out over a range of magnesium concentrations to determine the optimal magnesium concentration. The optimal magnesium concentration can vary depending on the nature of the target NDM1, KPC, IMP, VIM or OXA nucleic acid and the primers being used, among other parameters.

Deoxynucleotide Triphosphate Concentration

Deoxynucleotide triphosphates (dNTPs) are added to the reaction to a final concentration of from about 20 µM to about 300 µM. Typically, each of the four dNTPs (G, A, C, T) are present at equivalent concentrations (see, e.g., Innis et al., supra). In some embodiments, uracil N-glycosylase is used with dUTP (instead of TTP) in PCR reactions.

Nucleic Acid Polymerases

A variety of DNA dependent polymerases are commercially available that will function using the present methods and compositions. For example, Taq DNA Polymerase may be used to amplify target DNA sequences. The PCR assay may be carried out using as an enzyme component a source of thermostable DNA polymerase suitably comprising Taq DNA polymerase which may be the native enzyme purified from Thermus aquaticus and/or a genetically engineered form of the enzyme. Other commercially available polymerase enzymes include, e.g., Taq polymerases marketed by Qiagen, New England Biolabs, Applied Biosystems, Promega or Pharmacia. Other examples of thermostable DNA polymerases that could be used in the invention include DNA polymerases obtained from, e.g., *Thermus* and *Pyrococcus* species. Concentration ranges of the polymerase may range from 1-5 units per reaction mixture. The reaction mixture is typically between about 5 µl and about 100 µl.

Other Agents

Additional agents are sometimes added to the reaction to achieve the desired results. For example, DMSO can be added to the reaction, but is reported to inhibit the activity of Taq DNA Polymerase. Nevertheless, DMSO has been recommended for the amplification of multiple target sequences in the same reaction (see, e.g., Innis et al., supra). Stabilizing agents such as gelatin, bovine serum albumin, and non-ionic detergents (e.g., Tween-20) are commonly added to amplification reactions (see, e.g., Innis et al., supra). Additionally, betaine (Sigma-Aldrich; St. Louis, Mo.), an isostabilizing agent, can be added to equalize the contribution of GC- and AT-base pairing to the stability of the nucleic acid duplex.

Minor Groove Binders

Minor groove binder oligonucleotide conjugates (or "probes") are described in, e.g., U.S. Pat. No. 6,312,894. These conjugates form hyper-stabilized duplexes with complementary DNA. In particular, sequence specificity of short minor groove binder probes is excellent for high temperature applications such as PCR. The probes/conjugates of the present invention will also optionally have a covalently attached minor groove binder. A variety of suitable minor groove binders have been described in the literature (see, e.g., U.S. Pat. No. 5,801,155; Wemmer et al., Curr. Opin. Struct. Biol., 7:355-361 (1997); Walker et al., Biopolymers, 44:323-334 (1997); Zimmer et al., U. Prog. Biophys. Molec. Bio., 47:31-112 (1986); and Reddy et al., J. W., Pharmacol. Therap., 84:1-111 (1999)).

The minor groove binder-quencher-oligonucleotide-fluorophore conjugates can be in a linear arrangement (as suggested by the formula 5'-M-Q-ODN-F1-3' or 5'-M-F1-ODN-Q-3') or in a branched arrangement wherein the quencher (Q) and the minor groove binder (M or MGB) are attached to a linking group that serves to join ODN, Q, and M (or MGB). Additionally, the quencher can be attached at the distal (relative to attachment to ODN) terminus of the minor groove binder (e.g., 5'-Q-M-ODN-F1-3'). Each Of the arrangements is meant to be included when the linear abbreviation (M-Q-ODN-F1) is used. Additionally, the minor groove binder and quencher portions each can be attached at either the 3' or 5' end of the oligonucleotide, or an internal position of the oligonucleotide, so long as such attachment does not interfere with the quenching mechanisms of the conjugate. Generally, this can be accomplished through the use of a suitable linking group (see, e.g., U.S. Pat. Nos. 7,205,105 and 7,381,818).

Suitable methods for attaching minor groove binders (as well as reporter groups such as fluorophores and quenchers described below) through linkers to oligonucleotides are described in, for example, U.S. Pat. Nos. 5,512,677; 5,419,966; 5,696,251; 5,585,481; 5,942,610; and 5,736,626.

The minor groove binder is generally attached to the 3' or 5' position of the oligonucleotide portion via a suitable linking group. Attachment at the 5' end provides both a benefit of hybrid stability, since melting of an oligonucleotide duplex begins at the termini, but also reduces and/or prevents nuclease digestion of the probe during amplification reactions.

The location of a minor groove binder within a minor groove binder-oligonucleotide conjugate can also affect the discriminatory properties of such a conjugate. An unpaired region within a duplex will result in changes in the shape of the minor groove in the vicinity of the mispaired base(s). Since minor groove binders fit best within the minor groove of a perfectly-matched DNA duplex, mismatches resulting in shape changes in the minor groove would reduce binding strength of a minor groove binder to a region containing a mismatch. Hence, the ability of a minor groove binder to stabilize such a hybrid would be decreased, thereby increasing the ability of a minor groove binder oligonucleotide conjugate to discriminate a mismatch from a perfectly matched duplex. On the other hand, if a mismatch lies outside of the region complementary to a minor groove binder oligonucleotide conjugate, discriminatory ability for unconjugated and minor groove binder-conjugated oligonucleotides of equal length is expected to be approximately the same. Since the ability of an oligonucleotide probe to discriminate single base pair mismatches depends on its length, shorter oligonucleotides are more effective in discriminating mismatches. The primary advantage of the use of minor groove binder oligonucleotides conjugates in this context lies in the fact that much shorter oligonucleotides compared to those used in the prior art (i.e., 20 mers or shorter), having greater discriminatory powers, can be used, due to the pronounced stabilizing effect of minor groove binder conjugation.

The selection of minor groove binders and available minor groove binders have been disclosed in U.S. Pat. Nos. 5,801,155, 6,312,894 and 7,582,739.

Quenchers

Recently developed detection methods employ the process of fluorescence resonance energy transfer (FRET) for the detection of probe hybridization rather than direct detection of fluorescence intensity. In this type of assay, FRET occurs between a donor fluorophore (reporter) and an acceptor molecule (quencher) when the absorption spectrum of the quencher molecule overlaps with the emission spectrum of the donor fluorophore and the two molecules are in close proximity. The excited-state energy of the donor fluorophore is transferred to the neighboring acceptor by a resonance dipole-induced dipole interaction, which results in quenching of the donor fluorescence. If the acceptor molecule is a fluorophore, its fluorescence may sometimes be increased. The efficiency of the energy transfer between the donor and acceptor molecules is highly dependent on distance between the molecules. Equations describing this relationship are known. The Forster distance (Ro) is described as the distance between the donor and acceptor molecules where the energy transfer is 50% efficient. Other mechanisms of fluorescence quenching are also known, such as collisional and charge transfer quenching. There is extensive guidance in the art for selecting quencher and fluorophore pairs and their attachment to oligonucleotides (see, e.g., Haugland, Handbook of Fluorescent Probes and Research Chemicals, Ninth Edition, Molecular Probes, Eugene, Oreg. (2002) and the Web Edition at www.probes.com/handbook; and U.S. Pat. Nos. 3,996,345 and 4,351,760). Preferred quenchers are described in U.S. Pat. Nos. 6,727,356 and 6,790,945. Additional mono- and bis-azo dyes are commercially available from Berry and Associates (Dexter, Mich.) and Glen Research (Sterling, Va.).

Fluorophores

Fluorophores useful in the present invention are generally fluorescent organic dyes that have been derivatized for attachment to the terminal 3' or 5' carbon of the oligonucleotide probe, preferably via a linking group. One of skill in the art will appreciate that suitable fluorophores are selected in combination with a quencher that is typically also an organic dye, which may or may not be fluorescent. Examples of these and other suitable dye classes can be found in Haugland et al., Handbook of Fluorescent Probes and Research Chemicals, Sixth Ed., Molecular Probes, Eugene, Oreg. (1996); U.S. Pat. Nos. 3,194,805; 3,128,179; 5,187,288; 5,188,934; 5,227,487, 5,248,782; 5,304,645; 5,433,896; 5,442,045; 5,556,959; 5,583,236; 5,808,044; 5,852,191; 5,986,086; 6,020,481; 6,162,931; 6,180,295; and 6,221,604; EP Patent No. 1408366; Still other dyes are provided via online sites such as http://www.zeiss.com. Preferred phosphonate dyes are disclosed in co-owned U.S. Pat. Nos. 7,671,218, 7,767,834 and 8,163,910.

There is a great deal of practical guidance available in the literature for selecting appropriate fluorophore-quencher pairs for particular probes. Haugland supra and the Web Edition at www.probes.com/handbook and the like. Examples of these and other suitable dye classes can be found in Haugland et al., Handbook of Fluorescent Probes and Research Chemicals, Sixth Ed., Molecular Probes, Eugene, Oreg. (1996); U.S. Pat. Nos. 3,194,805; 3,128,179; 5,187,288; 5,188,934; 5,227,487, 5,248,782; 5,304,645; 5,433,896; 5,442,045; 5,556,959; 5,583,236; 5,808,044; 5,852,191; 5,986,086; 6,020,481; 6,162,931; 6,180,295; and 6,221,604; EP Patent No. 1408366; Still other dyes are provided via online sites such as http://www.zeiss.com. Methods for derivatizing fluorophores and quenchers for covalent attachment via common reactive groups are well known. See, for example, Haugland, supra; and U.S. Pat. Nos. 3,996,345 and 4,351,760.

Preferred fluorophores are those based on xanthene dyes, a variety of which are available commercially with substituents useful for attachment of either a linking group or for direct attachment to an oligonucleotide. Most preferred phosphonate dyes are disclosed in co-owned U.S. Pat. Nos. 7,671,218, 7,767,834 and 8,163,910.

EXAMPLES

The following examples are provided to illustrate, but not to limit, the subject matter described herein.

Oligonucleotides

Primers were synthesized using standard phosphoramidite chemistry. The 5'-M-F1-ODN-Q and F1-ODN-Q-M probes were prepared by automated DNA synthesis on a M-FL- or M-Q-modified polystyrene solid support, respectively, using 5-β-cyaoethyl- or 3'-β-cyanoethyl phosphoramidites (Glen Research; Sterling, Va.) designed for synthesis of oligonucleotide segments in the 5'→3 or 3'→5' direction, respectively. Oligonucleotide synthesis was performed on an ABI 394 synthesizer according to the protocol supplied by the manufacturer using a 0.02M iodine solution. Modified and universal bases were synthesized based on the methods disclosed in U.S. Pat. Nos. 6,949,367, 6,127,121 and U.S. Patent Publication No. 20120244535. Fluorophore reporting dyes or quenchers were introduced at the last step of the synthesis using the corresponding phosphoramidites as required. All oligonucleotides were purified by reverse phase HPLC.

PCR

Real-time PCR was performed using the RGQ MDx real-time PCR amplification instrumentation on samples from human rectal swabs from symptomatic and asymptomatic patients material extracted with QIAsymphony SP/AS DNA extraction system (QIAGEN Inc., Valencia, Calif.) in a diagnostic assay to detect ESBL DNA. The assay mixture contains the following components:

Master Solution A: CRE Master A: Includes the KPC-, IMP-, VIM-, NDM-, Oxa-48-, and Oxa-181-specific and Internal Control probes and primers, PCR buffer, HotStart-Taq QR2 DNA Polymerase, Uracil N-Glycosylase, and deoxynucleotides (dATP, dCTP, dGTP, and dUTP). 23 μL of the CRE Master A reagent mix will be used for each 40 μL PCR reaction. The formulation of CRE Master A was selected as shown in Table 7 below.

TABLE 7

Primers, Probes and Reagents Composition of Master Solution A.

| SEQ ID NO: | Name | Sequence 5'-3' | 1X [μM] |
|---|---|---|---|
| 1 | KPC-FAM-1 | $R_{a1}$-G*CAGGTTCCGGTTTTG-$R_{b1}$ | 0.10 μM |
| 2 | KPC-L1 | AATAAATCATGTCATTTGCCGTGCCATAC | 0.50 μM |
| 3 | KPC-E1 | AATAAATCATAAGCAGACTGGGCAGTCGG | 0.50 μM |
| 4 | IMP-AP593-4 | $R_{a2}$-G*GI*CACACTCCAGATAAC-$R_{b1}$ | 0.10 μM |
| 5 | IMP-AP593-5 | $R_{a2}$-G*GI*CACACTCAAGATAAC-$R_{b1}$ | 0.10 μM |
| 6 | IMP-AP593-15 | $R_{a2}$-G*CTGA*A*TTAA*CI*AATGAGC-$R_{b1}$ | 0.10 μM |
| 7 | IMP-AP593-16 | $R_{a2}$-G*CTGA*A*TTAA*CI*AATGAAC-$R_{b1}$ | 0.10 μM |
| 8 | IMP-L1 | AATAAATCATGGAATA*GAGTGGCTTAATTCTC | 0.50 μM |
| 9 | IMP-L2 | AATAAATCATGGAATA*GGGTGGCTTAATTCTC | 0.50 μM |
| 10 | IMP-L3 | AATAAATCATGGAATA*GAATGGCHAACTCTC | 0.50 μM |
| 11 | IMP-E7 | AATAAATAGGCAACCAAACCACTACGTTATCT | 0.50 μM |
| 12 | IMP-E8 | AATAAATAGGCAGCCAAACTACTAGGTTATCT | 0.50 μM |
| 13 | VIM-AP593-7 | $R_{a2}$-G*TGCGCTTCGGTCC-$R_{b1}$ | 0.10 μM |
| 14 | VIM-L4 | AATAACGCATTCTCTAGAAGGACTCTCATC | 0.50 μM |
| 15 | VIM-L6 | AATAACGCACTCTCTAAAAGCGCTCTCCTC | 0.50 μM |
| 16 | VIM-E6 | AATAAATCACGAATGCGCAGCACCI*GGATAGA | 0.50 μM |
| 17 | NDM-AP593-2 | $R_{a2}$-G*ACATGCCGGGTTTC-$R_{b1}$ | 0.10 μM |
| 18 | NDM-L2 | AATAAATCATAAGTCTGGCAGCACACTTCCTA | 0.50 μM |
| 19 | NDM-E2 | AATAAATCATAACGCCATCCCTGACGATCAAAC | 0.50 μM |
| 20 | OXA-AP662-7 | $R_{a1}$-G*TGTTTTTGGTGGCATCG-$R_{b1}$ | 0.20 μM |
| 21 | OXA-L1 | AATAAATCAATGCGTGTATTAGCCTTATCGGC | 1.00 μM |
| 22 | OXA-E1 | AATAAATCATTCTTGCCATTCCTTTGCTACCG | 0.250 μM |
| 23 | E6132-L | CTGCACGGACCAGTTACTTTACG | 0.20 μM |
| 24 | E6132-E | CTCATTTTTTCTACCGGAGATCTTGT | 0.20 μM |
| 25 | E6132-AP525-TM3 | $R_{a4}$-G*ACCACGTACCGCATTG-$R_{b1}$ (MGB phosphoramidite) | 0.10 μM |
| 26 | OXA-Qzr705-1 | $R_{a5}$-G*GTGGCATCGATTATC-$R_{b2}$ | 0.10 μM |
| 27 | OXA-AP662-7 | $R_{a6}$-G*TGTTTTTGGTGGCATCG-$R_{b3}$ | 0.10 μM |
|  | 100 mM dATP | N/A | 0.200 mM |
|  | 100 mM dCTP | N/A | 0.200 mM |
|  | 100 mM dGTP | N/A | 0.200 mM |

TABLE 7-continued

Primers, Probes and Reagents
Composition of Master Solution A.

| SEQ ID NO: | Name | Sequence 5'-3' | 1X [µM] |
|---|---|---|---|
| | 100 mM dUTP | N/A | 0.400 mM |
| | 10X PCR Buffer | N/A | 1X |
| | HotStarTaq QR2 DNA Polymerase | 5 U/µL | 0.10 U/µL |
| | UNG | 1 U/µL | 0.01 U/µL |
| | Molecular Biology Grade Water | N/A | N/A |

Where G* = Super G;
A* = Super A,
I* = 3-aminobutynyl-1H-pyrazolo[3,4-d]pyrimidin-4(5H)-one;
$R_{a1}$ = FAM;
$R_{a2}$ = AP593;
$R_{a3}$ = AP662;
$R_{a4}$ = AP525;
$R_{a5}$ = Quasar 705 (Biosearch Technology, Petaluma, CA);
$R_{a6}$ = MGB-$R_{a3}$;
$R_{b1}$ = Eclipse® Dark Quencher-MGB;
$R_{b2}$ = Quencher575-MGB and
$R_{b3}$ = Eclipse® Dark Quencher.
Quencher575 = (E)-4-((4-((2-chloro-4-nitrophenyl)diazenyl)-2,5-dimethoxyphenyl)(ethyl)amino)butanoic acid.
AP = AquaPhlour Dye-IW with emission wavelength (IW) noted.
Lower case represents flap sequences.

Master Solution B: an 80 mM MgCl$_2$ solution. 2 µL of the Master B reagent mix is used for each 40 µL PCR reaction for the final concentration of 4 mM.

Sample: 15 µL of the extracted sample.

Figure 3:
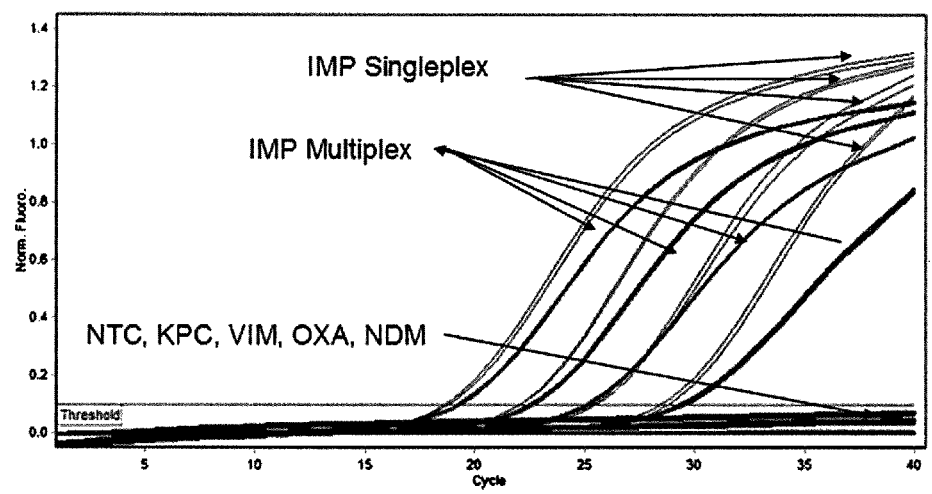
FIG. 3 shows the real-time PCR detection of IMP gene target with a TaqMan probe in the presence and absence of KPC, VIM, OXA, NDM and NTC targets.

The PCR cycling profile is shown in FIG. 3 and described below in Table 8.

TABLE 8

PCR Cycling Profile

| Stage | Temp (° C.) | Time |
|---|---|---|
| UNG Treatment Polymerase Activation | 50° C. | 2 min. |
| UNG Deactivation | 95° C. | 15 Min. |
| Denaturation: | 95° C. | 10 Sec. |
| Annealing: | 56° C. | 30 Sec. |
| Extension: | 72° C. | 15 Sec. |

Example 1

This example illustrates the specific amplification and detection of Oxa48/Oxa181 gene targets with 10 fold titration from $10^3$ to $10^6$ copies using amplification primers SEQ ID NO: 21 and 22 and detecting TaqMan MGB (SEQ ID NO:26) or Pleiades (SEQ ID NO:27) probes in FIGS. 1(a) and 1(b), respectively.

The assays were performed in duplicate, in singleplex and in multiplex with 2000 copies internal control (IC) utilizing primers SEQ ID NO: 23 and 24 and probe SEQ ID NO: 25 as described above, detecting the amplified Oxa48/Oxa181 gene targets with probes ID NO: 26 and 27 respectively. The results are shown in FIG. 1(c).

Example 2

This example illustrates the specific amplification and detection of KPC gene targets with 10 fold titration from $10^3$ to $10^6$ copies with a TaqMan MGB probe.

Figure 2:
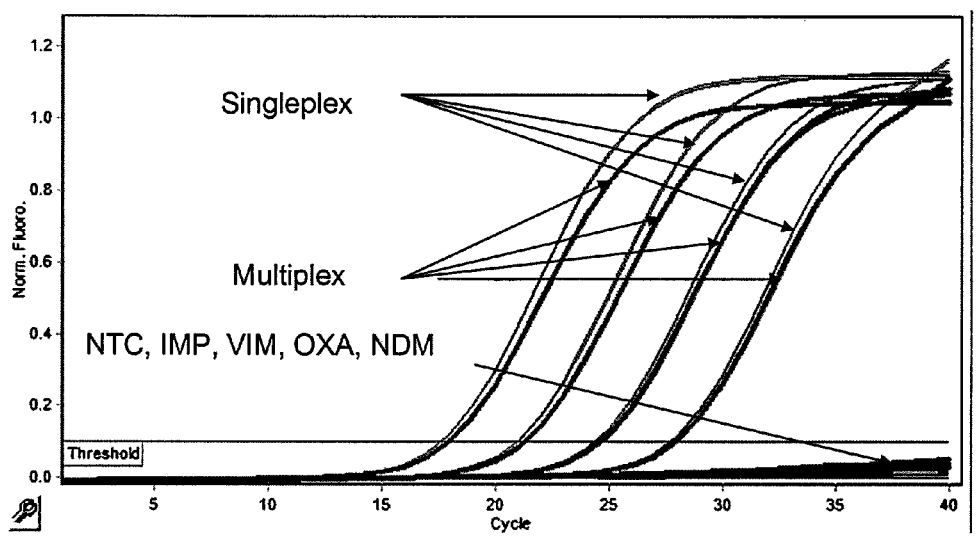
FIG. 2 shows the real-time PCR detection of KPC gene targets with a TaqMan probe.

The assays were performed in duplicate, in singleplex and in multiplex with 2000 copies internal control (IC) as described above in Example 1. The KPC gene target was amplified with primers having SEQ ID NOs: 2 and 3 in the presence of NTC, IMP, VIM, OXA and NDM gene targets, and the amplified KPC targets were specifically detected with a probe having SEQ ID NO: 1. The results are shown in FIG. 2.

Example 3

This example illustrates the specific amplification and detection of IMP gene targets with 10 fold titration from $10^3$ to $10^6$ copies with a TaqMan MGB probe in the presence of NTC, KPC, VIM, OXA and NDM gene targets.

The assays were performed in duplicate, in singleplex and in multiplex with 2000 copies internal control (IC) as described above. The IMP gene target was amplified with primers having SEQ ID NOs: 8 to 12, and the amplified IMP targets were detected with probes having SEQ ID NOs: 4 to 7. The results are shown in FIG. 3. As shown in FIG. 3, no dye spill over is seen between the detection dyes.

Example 4

Figure 4:
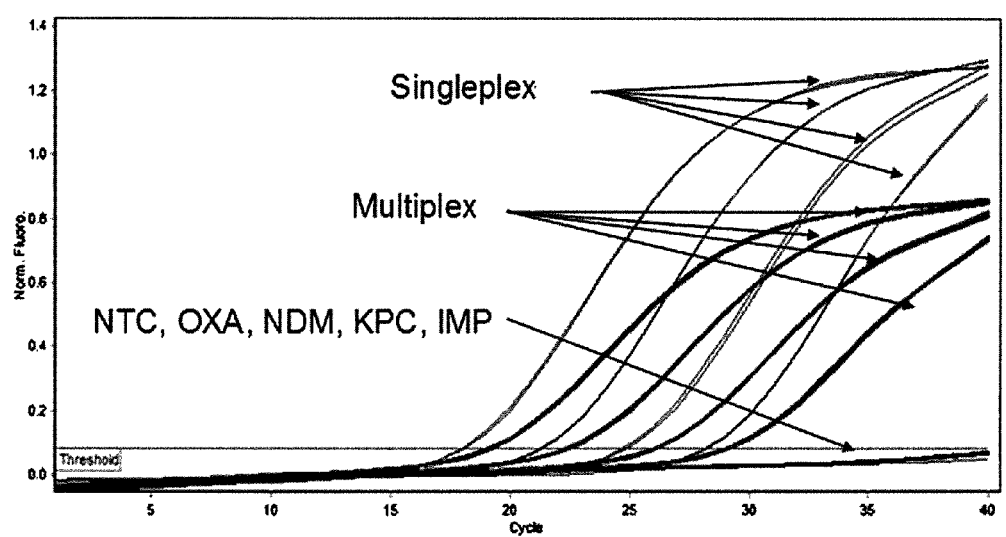
FIG. 4 shows the real-time PCR detection of VIM gene target with a TaqMan probe in the presence and absence of KPC, IMP, OXA, NDM and NTC gene targets.

This example illustrates the specific amplification and detection of VIM gene targets with 10 fold titration from 103 to 106 copies with a TaqMan MGB probe in the presence of NTC, KPC, IMP, OXA and NDM gene targets. The assays were performed in duplicate, in singleplex and in multiplex as described above. The VIM gene target was amplified with primers having SEQ ID NOs: 14 to 16, and the amplified VIM targets were detected with a probe having SEQ ID NO: 13. The results ware shown in FIG. 4.

Example 5

Figure 5:
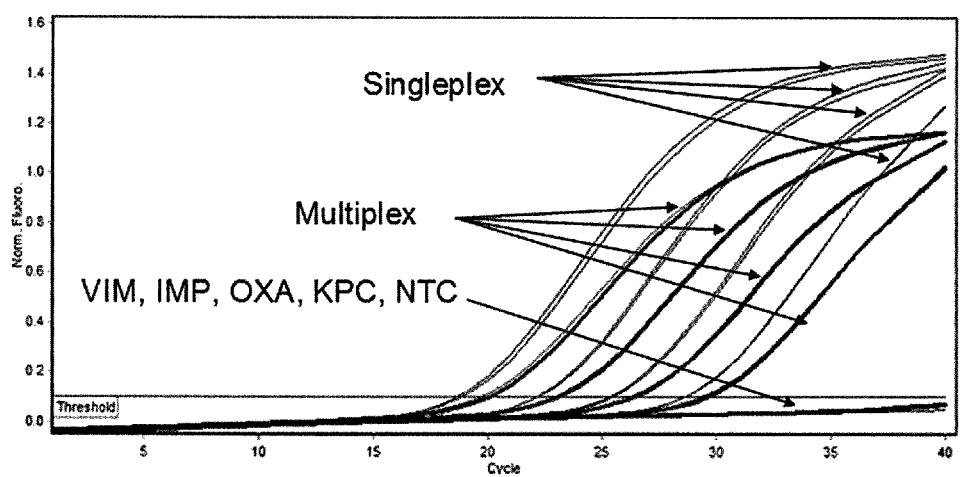
FIG. 5 shows the real-time PCR detection of NDM-1 gene target with a TaqMan probe in the presence and absence of KPC, IMP, OXA, VIM and NTC gene targets.

This example illustrates the specific amplification and detection of NDM1 gene targets with 10 fold titration from $10^3$ to $10^6$ copies with a TaqMan MGB probe in the presence of NTC, KPC, VIM, OXA and VIM gene targets. The assays were performed in duplicate, in singleplex and in multiplex as described above. The NDM1 gene target was amplified with primers having SEQ ID NOs: 18 and 19, and the amplified NDM1 gene targets were detected with a probe having SEQ ID NO: 17. The results are shown in FIG. 5.

Example 6

This example illustrates the multiplex detection of KPC, IMP, VIM, NDM, OXA and IC targets labeled with four different dyes.

Figure 6:
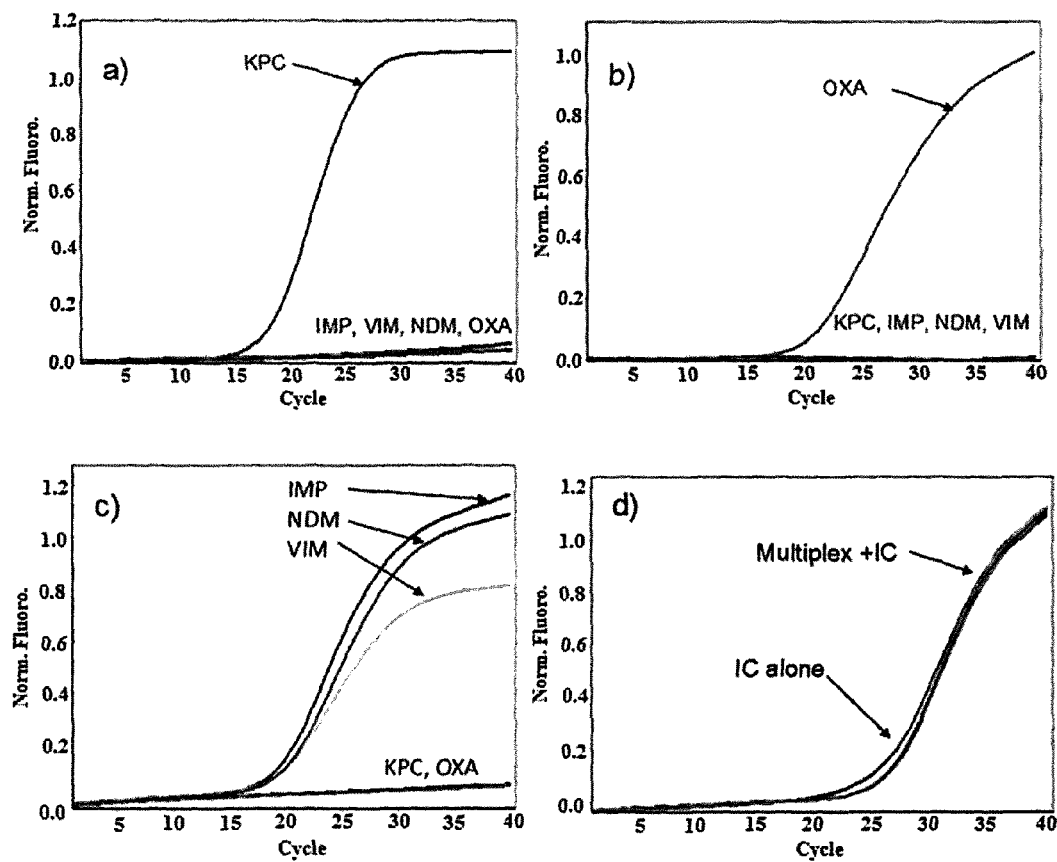
FIG. 6 shows (a) the detection of amplified KPC target in the presence of IMP, VIM, NDM and OXA targets with FAM labeled TaqMan Probe; (b) the detection of amplified OXA target in the presence of KPC, IMP, VIM, and NDM targets with a Qzr705-labeled probe; (c) the detection of IMP, VIM and NDM targets in the presence of KPC and OXA targets with -AP593-labeled probes; and (d) the detection of the IC target alone or in multiplex in the presence of KPC, IMP, VIM, OXA and NDM targets with a AP525-labeled probe.

The individual targets were present at $10^6$ copies and the internal control at 2000 copies per reaction. The amplified targets of KPC, IC and OXA were detected with probes labeled with FAM, AP525 and Quazer705, respectively. The amplified IMP, VIM and NDM targets were detected with AP593-labeled probes. The multiplex real-time amplification and detection results are shown in FIG. 6.

The results in FIG. 6(a)-6(d) clearly demonstrate that none of the four different dyes used for detection of amplified targets in four different wave length detection channels show any fluorescence bleed-over between the different detection fluorescent channels.

Example 7

Figure 7:
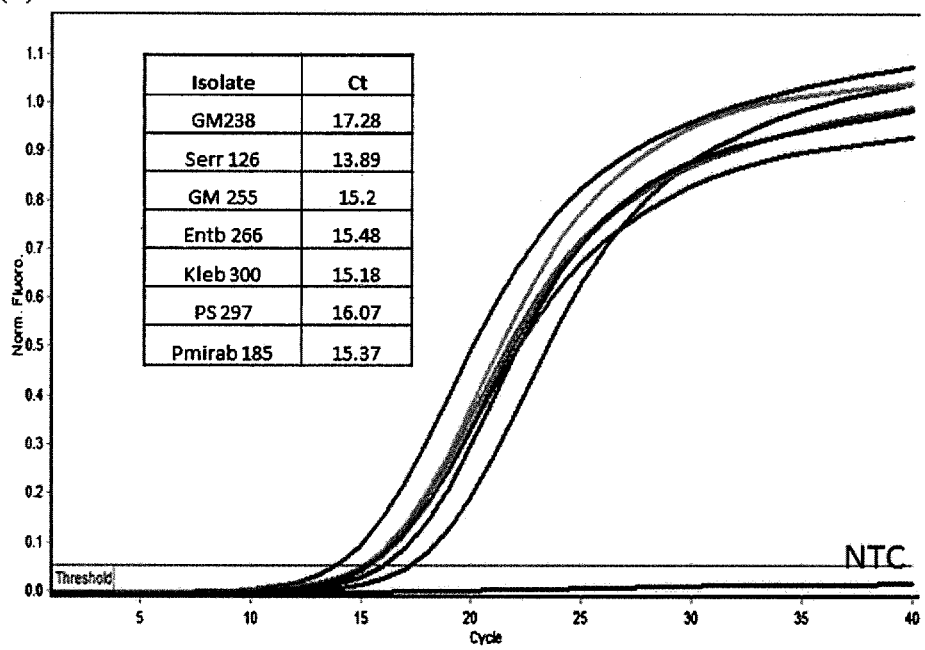
FIG. 7 shows (a) the detection of amplified targets for seven bacterial isolates using IMP probes (SEQ ID NOS: 4-7) and primers (SEQ ID NOS: 9-12) in real-time PCR with Cts associated with each isolate; and (b) gel analysis of the PCR fractions for each bacterial strain.
Figure 7:
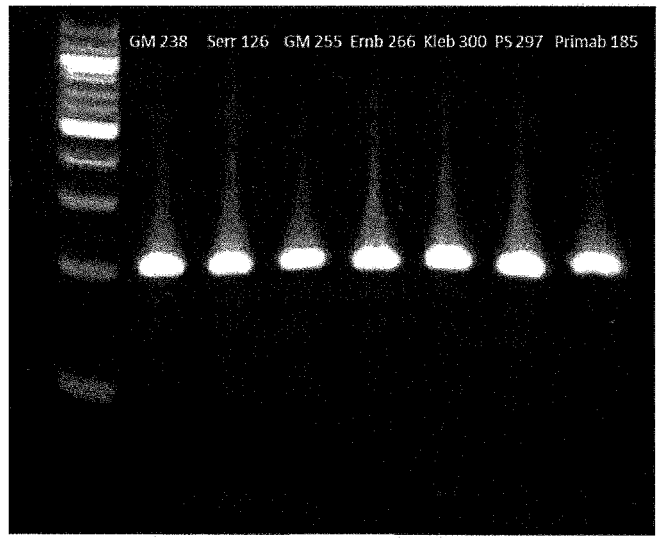

This example illustrates the results of assays for the detection of DNA extracted from seven bacterial isolates (National Collection of Type Cultures [NCTC], Public Health England) using IMP probes (SEQ ID NOS: 4-6) and primers (SEQ ID NOS: 7-12). 10 ng DNA of each isolate was used. The real-time amplification and detection results are shown in FIG. 7(a), with the agarose gel analysis of one assay shown in FIG. 7(b). The results clearly demonstrate that primers and probes successfully detect seven commonly occurring IMP containing bacterial isolates in real-time. Real-time curves in FIG. 7(a) can be identified from the position of the Ct listed. The gel in FIG. 7(b) confirms the specific PCR amplification of seven strains yielding amplicons with the same length.

Example 8

Figure 8:
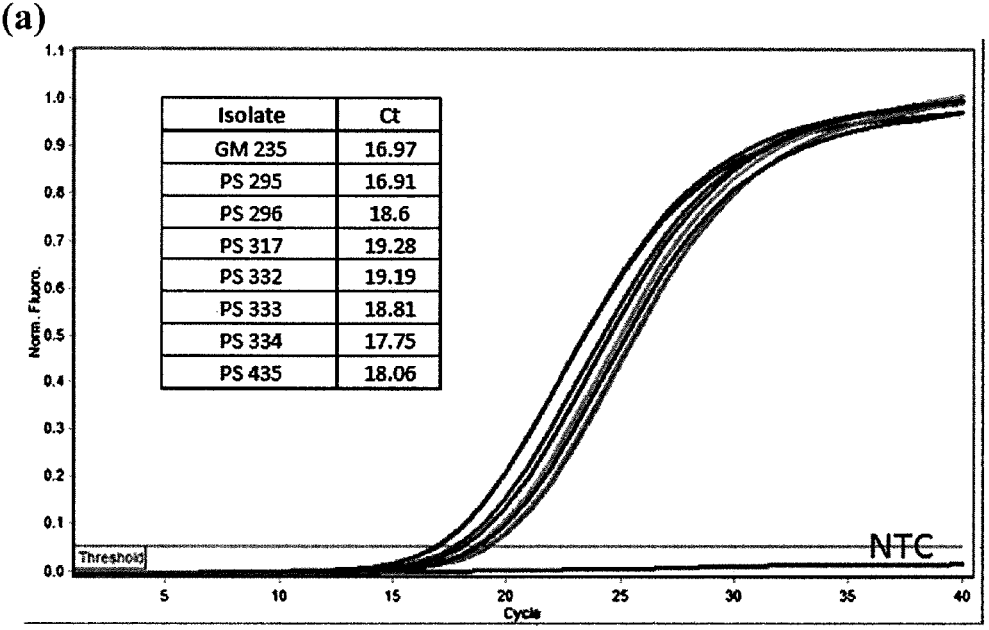
FIG. 8 shows (a) the detection of amplified targets for eight bacterial isolates using a VIM probe (SEQ ID NO:13) and primers (SEQ ID NOS: 14-16) with Cts associated with each isolate; and (b) gel analysis of the PCR fractions for each bacterial strain.
Figure 8:
Figure 9:
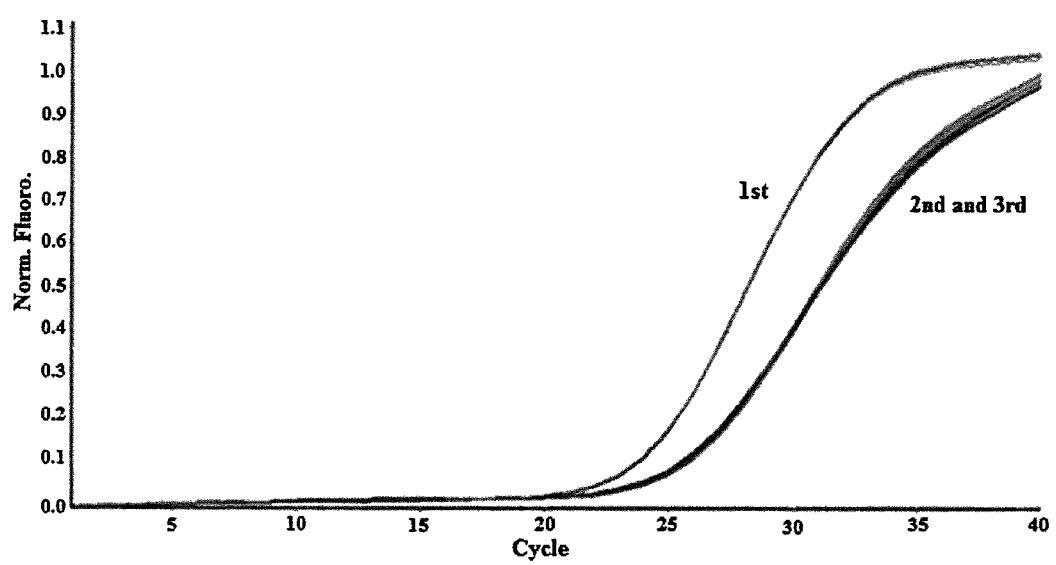
FIG. 9 shows the detection of amplified targets using KPC primers (SEQ ID NOS: 2, 3, 34-36, 39, and 40) and probes (SEQ ID NOS: 1, 37, 38, 42, and 43) in three locations within the KPC sequence.
Figure 10:
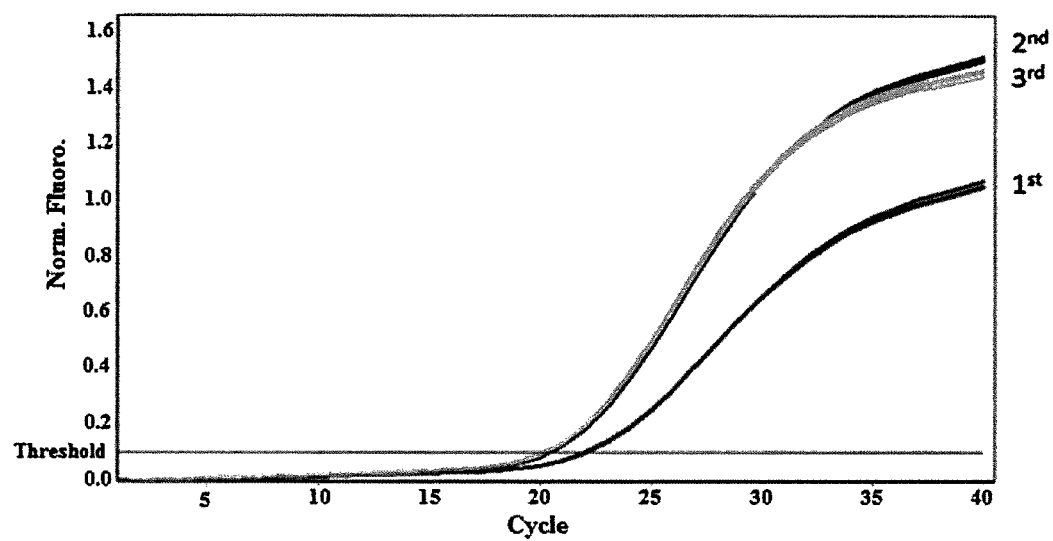
FIG. 10 shows the detection of amplified targets using NDM primers (SEQ ID NOS: 18, 19, 66, 67, 69, and 70) and probes (SEQ ID NOS: 17, 68, and 71) in three locations within the NDM sequence.
Figure 11:
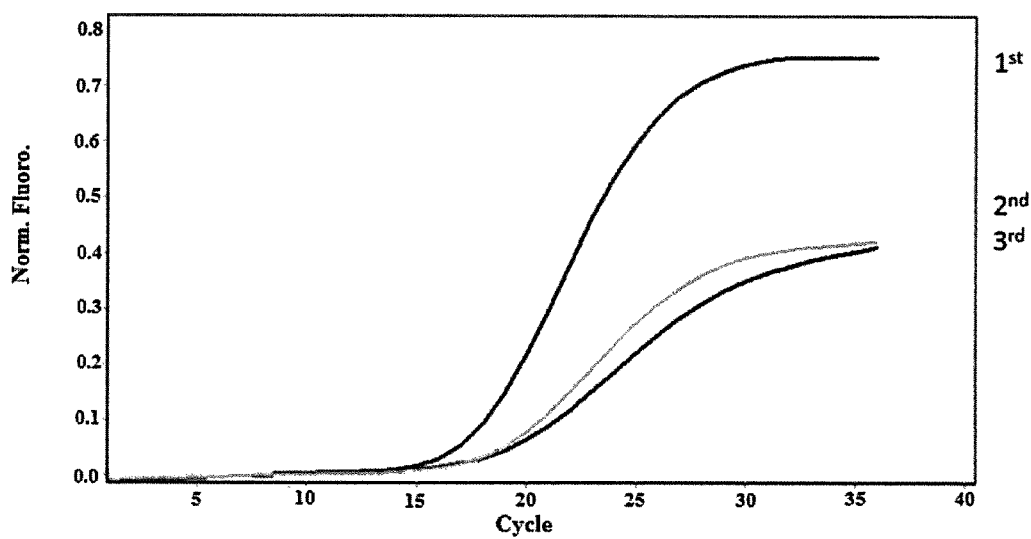
FIG. 11 shows the detection of amplified targets using OXA-48 primers (SEQ ID NOS: 21, 22, 72, 73, 75, and 76) and probes (SEQ ID NOS: 20, 74, 77, and 78) in three locations within the OXA-48 sequence.

This example illustrates the results of assays for the detection of DNA extracted from eight bacterial isolates (National Collection of Type Cultures [NCTC], Public Health England) using a VIM probe (SEQ ID NO: 13) and primers (SEQ ID NOS: 14-16). 10 ng DNA of each isolate was used. The real-time amplification and detection results are shown in FIG. 8(a), with the agarose gel analysis of one assay shown in FIG. 8(b). The results clearly demonstrate that primers and probes successfully detect eight commonly occurring VIM containing bacterial isolates in real-time. Real-time curves in FIG. 8(a) can be identified from the position of the Ct listed. The gel in FIG. 8(b) confirms the specific PCR amplification of eight VIM strains yielding amplicons with the same length.

Example 9

The PCR reactions were dispensed, run, and analyzed using an ELITe InGenius® instrument (ElitechGroup Molecular Diagnostics, Bothell, Wash.) with conditions listed in Table 9 below. Instrument operation followed ELITechGroup "ELITe InGenius Instructions for Use" (INT030). All monoreagents were prepared using primers, probes, and reagents to the final concentrations listed in Table 10. Monoreagents were stored on the InGenius instrument's cold block. Samples were placed in the InGenius instrument eluate position #1. Necessary tips were loaded on the InGenius instrument. Using the InGenius instrument software, the run was performed by indicating the monoreagent and sample positions in the graphical user interface using the stored assay containing parameters described in Table 9. The InGenius instrument then set up the PCR reaction with its robotic pipettor, and automatically analyzed the assay once completed.

TABLE 9

| PCR Cycling Parameters | | |
|---|---|---|
| Stage | Temp (° C.) | Time |
| Precycle | 95° C. | 15 Min. |
| Denaturation: | 95° C. | 10 Sec. |
| Annealing: | 56° C. | 30 Sec. |
| Extension: | 72° C. | 15 Sec. |

All monoreagents were prepared using primers, probes, and reagents to the final concentrations listed in Table 10 below.

TABLE 10

Primers, Probes and Reagents Composition

| SEQ ID NO | Component | Final Conc | Sequence |
|---|---|---|---|
|  | OXA probe | 0.174 µM | See Table 11 below |
| 21 | OXA-L1 | 0.870 µM | AATAAATCAATGCGTGTATTAGCCTTATCGGC |
| 22 | OXA-E1 | 0.870 µM | AATAAATCATTCTTGCCATTCCTTTGCTACCG |
| 23 | E6132-L | 0.348 µM | CTGCACGGACCAGTTACTTTACG |
| 24 | E6132-E | 0.348 µM | CTCATTTTTTCTACCGGAGATCTTGT |
| 25 | E6132-AP525-TM3 | 0.174 µM | 417-G*ACCACGTACCGCATTG-Z28-577 |
|  | 100 mM dATP | 0.348 mM |  |
|  | 100 mM dCTP | 0.348 mM |  |
|  | 100 mM dGTP | 0.348 mM |  |

TABLE 10-continued

Primers, Probes and Reagents Composition

| SEQ ID NO | Component | Final Conc | Sequence |
|---|---|---|---|
|  | 100 mM dTTP | 0.348 mM |  |
|  | QR2 HotStarTaq | 0.174 U/μM |  |
|  | 1XTE, pH 8.0 | 0.1205X |  |

TABLE 11

Pleiades and TaqMan Probes with different fluorophores.

| SEQ ID NO | OXA Probe | Sequence |
|---|---|---|
| 79 | OXA-PBI1 | MGB-AP662-G*ATAATCGATGCCACCAAA-EDQ |
| 80 | OXA-PBI2 | MGB-AP662-G*ATAATCGATGCCACCAAA-EDQ |
| 81 | OXA-PBI3 | MGB-AP680-G*ATAATCGATGCCACCAAA-EDQ |
| 82 | OXA-PBI4 | MGB-AP680-G*ATAATCGATGCCACCAAA-EDQ |
| 83 | OXA-Cy55-1 | Cy5.5-G*GTGGCATCGATTATC-EDQ-MGB |

Figure 12:
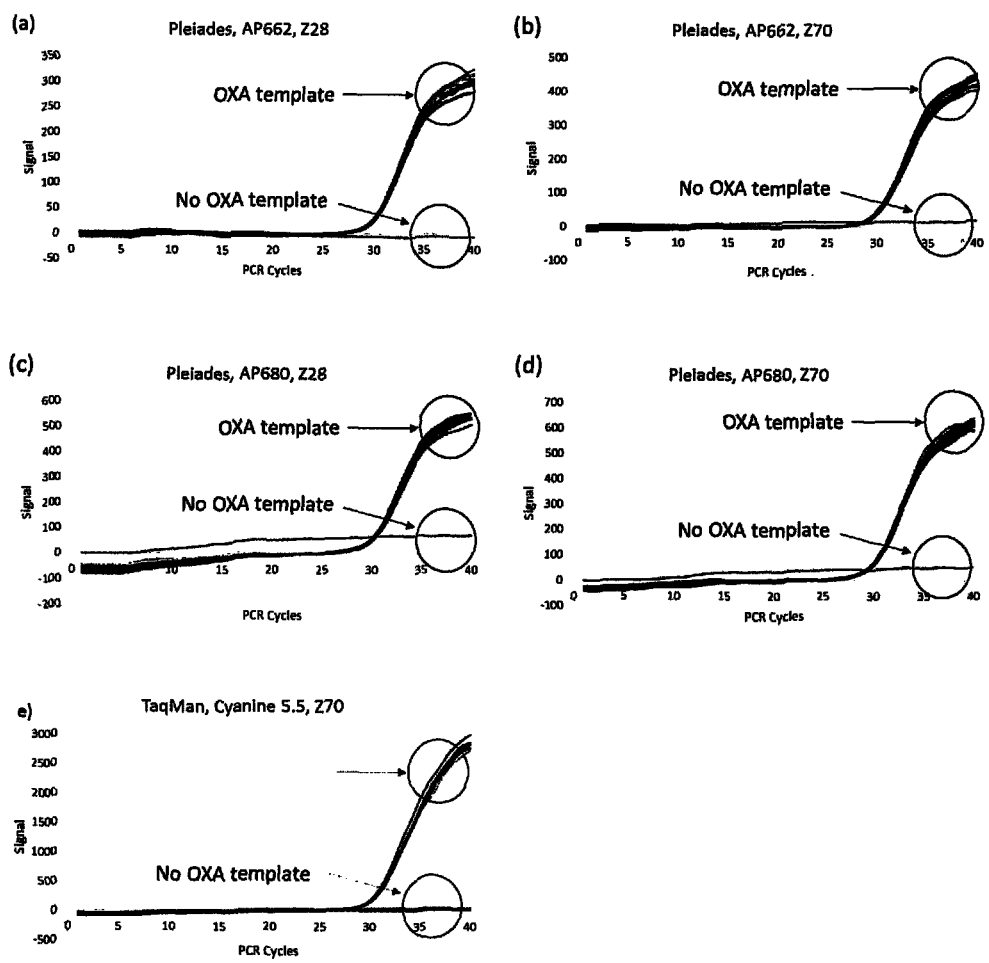
FIG. 12 shows the detection of amplified targets using OXA-48 primers (SEQ ID NOS: 21 and 22) and Pleiades and TaqMan probes labeled with different dyes, (a)-(e) SEQ ID NOS: 79-83.

The real-time PCR curves are shown for the Pleiades probes (SEQ ID NOS:79-82) in FIG. 12(a) to (d) and the TaqMan Probe (SEQ ID NO:83) in FIG. 12(e). This illustrates successful detection of OXA targets with both Pleiades and TaqMan Probes. Similar detection is also shown for the Pleiades probes labeled with different dyes.

REFERENCES CITED

The following documents and publications are hereby incorporated by reference.

U.S. and Foreign Patent Documents

EP Patent No. 1408366
PCT Patent Publication No.
WO 1999/37085
WO2012023054A2
WO 2013/078565
U.S. Patent Publication No.
2005-0118623
2007-0048758
2012-0244535
2009-0163382
2009-031780
2011-0190170
2012-0129180
2012-0244535
2012-0245219
U.S. Patent No.
U.S. Pat. No. 3,128,179
U.S. Pat. No. 3,194,805
U.S. Pat. No. 3,996,345
U.S. Pat. No. 4,351,760
U.S. Pat. No. 4,415,732
U.S. Pat. No. 4,458,066
U.S. Pat. No. 4,683,195
U.S. Pat. No. 4,739,044
U.S. Pat. No. 4,757,141
U.S. Pat. No. 4,965,188
U.S. Pat. No. 4,997,928
U.S. Pat. No. 5,187,288
U.S. Pat. No. 5,188,934
U.S. Pat. No. 5,227,487
U.S. Pat. No. 5,231,191
U.S. Pat. No. 5,248,782
U.S. Pat. No. 5,304,645
U.S. Pat. No. 5,433,896
U.S. Pat. No. 5,442,045
U.S. Pat. No. 5,508,178
U.S. Pat. No. 5,512,677
U.S. Pat. No. 5,538,848
U.S. Pat. No. 5,419,966
U.S. Pat. No. 5,556,959
U.S. Pat. No. 5,583,236
U.S. Pat. No. 5,585,481
U.S. Pat. No. 5,696,251
U.S. Pat. No. 5,736,626
U.S. Pat. No. 5,801,155
U.S. Pat. No. 5,808,044
U.S. Pat. No. 5,852,191
U.S. Pat. No. 5,925,517
U.S. Pat. No. 5,942,610
U.S. Pat. No. 5,986,086
U.S. Pat. No. 5,994,056
U.S. Pat. No. 6,020,481
U.S. Pat. No. 6,162,931
U.S. Pat. No. 6,127,121
U.S. Pat. No. 6,180,295
U.S. Pat. No. 6,221,604
U.S. Pat. No. 6,312,894
U.S. Pat. No. 6,653,473
U.S. Pat. No. 6,683,173
U.S. Pat. No. 6,727,356
U.S. Pat. No. 6,790,945
U.S. Pat. No. 6,905,848
U.S. Pat. No. 6,949,367
U.S. Pat. No. 6,972,339
U.S. Pat. No. 7,045,610
U.S. Pat. No. 7,205,105
U.S. Pat. No. 7,319,022
U.S. Pat. No. 7,381,818
U.S. Pat. No. 7,582,739
U.S. Pat. No. 7,662,942
U.S. Pat. No. 7,671,218
U.S. Pat. No. 7,759,126
U.S. Pat. No. 7,767,834
U.S. Pat. No. 7,790,385
U.S. Pat. No. 7,968,292
U.S. Pat. No. 8,163,910
U.S. Pat. No. 8,410,255

Non-Patent References

Agrawal et al., Tetrahedron Letters, 31:1543-1546 (1990)
Bengtsson et al., Nucl. Acids Res., 31: e45 (2003)
Bolli et al., Nucleic Acids Res., 24:4660-4667 (1996),
Capaldi, et al., Nuc. Acids Res., 28:E21 (2000)
Caruthers et al., Genetic Engineering, 4:1-17 (1982)

Dreier et al., J Clin Microbiol. 43(9):4551-7(2005)
Eckstein, (ed.), Oligonucleotides and Analogues: A Practical Approach, IRL Press, Oxford (1991)
Georgopapadakou N H. Expert Opin Investig Drugs. 23:145-8 (2014)
Giusti et al., PCR Methods and Applications, 2:223-227 (1993)
Haugland, Handbook of Fluorescent Probes and Research Chemicals, Ninth Edition, Molecular Probes, Eugene, Oreg. (2002) and the Web Edition at www.probes.com/handbook; Holten K B, Onusko E M American Family Physician 62 (3): 611-20 (2000)
Hoorfar et al. J Clin Microbiol.;42(5):1863-8 (2004).
Kutyavin et al., Nucl. Acids Res., 28: 655-661 (2000)
March et al., ADVANCED ORGANIC CHEMISTRY—Reactions, Mechanisms and Structures, 4th ed., John Wiley & Sons, New York, N.Y. (1992).
McPherson et al., PCR Basics, 2000; and Rapid Cycle Real-time PCR Methods and Applications: Quantification, Wittwer et al. (eds.), Springer-Verlag (2004))
Mullis et al., Cold Spring Harb. Symp. Quant. Biol., 51 Pt 1:263-273 (1986)
Nelson et al., Nuc. Acids Res., 17:7187-7194 (1989)
Nielsen et al., Science, 254:1497-1500 (1991)
Niemz, A. et al Trends Biotechnol., 29: 240-50 (2011)
Papagiannitsis et al., Antimicrob. Agents Chemother. 55: 3570-3572 (2011)
Perez F and Van Duin D., Cleve Clin J Med., 80: 225-33 (2013)
Picard et al., J Clin Microbiol. 47(3):751-7 (2009)
Poirel et al., Antimicrob. Agents Chemother. 56: 559-562 (2012)
Potron et al., Antimicrob. Agents Chemother. 55: 4896-4899 (2011)
Reddy et al., J. W., Pharmacol. Therap., 84:1-111 (1999)
Sharma et al., Nuc. Acids Res., 19:3019 (1991)
Samuelsen et al., J Antimicrob Chemother., 68: 1682-5 (2013)
Sproat et al., Nuc. Acids Res., 15:4837 (1987)
Users Manual Model 392 and 394 Polynucleotide Synthesizers, pages 6-1 through 6-22, Applied Biosystems, Part No. 901237 (1991).
Walker et al., Biopolymers, 44:323-334 (1997)
Wemmer et al., Curr. Opin. Struct. Biol., 7:355-361 (1997)
Yigit, et al., Antimicrob. Agents Chemother. 45 :1151-1161 (2001)
Yong et al, Antimicrob Agents Chemother. 53:5046-54 (2009)
Zimmer et al., U. Prog. Biophys. Molec. Bio., 47:31-112 (1986)
Zuckerman et al., Nuc. Acids Res., 15:5305-5321 (1987)

What is claimed is:

1. A method for detecting one or more NDM1, KPC, IMP, VIM and OXA resistance-encoding genes in a sample, comprising:
   (a) contacting a sample suspected of containing at least two of the NDM1, KPC, IMP, VIM and OXA resistance-encoding genes with at least two primers, wherein each primer comprises a sequence that is at least 85% complementary to at least one of any of the full-length sequences selected from SEQ ID NO: 2, 3, 8, 9, 10, 11, 12, 14, 15, 16, 18, 19, 21, 22, 34, 35, 36, 39, 40, 44, 45, 46, 47, 50, 51, 52, 53, 56, 57, 58, 59, 62, 63, 66, 67, 69, 70, 72, 73, 75, and 76 to produce a mixture;
   (b) incubating the mixture of step (a) under conditions sufficient to amplify NDM1, KPC, IMP, VIM or OXA target nucleic acids, thereby generating amplified nucleic acids; and
   (c) detecting in a single reaction the amplified NDM1, KPC, IMP, VIM or OXA target nucleic acids using different fluorescence-generating probes for each of the NDM1, KPC, IMP, VIM or OXA target nucleic acids, wherein the different fluorescence-generating probes comprise different fluorophores, and wherein each fluorescence-generating probe comprises a sequence that is at least 85% complementary to at least one of any of the full-length sequences selected from SEQ ID NO: 1, 4, 5, 6, 7, 13, 17, 20, 26, 27, 37, 38, 41, 42, 43, 48, 49, 54, 55, 60, 61, 64, 65, 68, 71, 74, 77, 78, 79, 80, 81, 82, and 83, wherein $R_a$ is a fluorophore with emission wavelength between about 400 and 900 nm, $R_b$ is a non-fluorescent quencher, and wherein substitution of $R_a$ and $R_b$ allows quenching of fluorescence when the probe is unhybridized.

2. The method of claim 1 wherein the amplified nucleic acids comprise at least a portion of at least two of the NDM1, KPC, IMP, VIM and OXA resistance-encoding genes.

3. The method of claim 1, wherein at least one fluorescence-generating probe further comprises a minor groove binder.

4. The method of claim 3, wherein the minor groove binder is attached to the 3' end of the fluorescence-generating probe.

5. The method of claim 3, wherein the minor groove binder is attached to the 5' end of the fluorescence-generating probe.

6. The method of claim 1, further comprising the step of amplifying a control nucleic acid having a sequence of SEQ ID NO: 33.

7. The method of claim 6, wherein the step of amplifying a control nucleic acid comprises using a fluorescence-generating probe that is at least 85% complementary to the full-length sequence of SEQ ID NO: 25, wherein $R_a$ is a fluorophore with emission wavelength between about 400 and 900 nm, $R_b$ is a non-fluorescent quencher, and wherein substitution of $R_a$ and $R_b$ allows quenching of fluorescence when the probe is unhybridized.

8. The method of claim 6, wherein the step of amplifying a control nucleic acid comprises using one or more primers that is at least 85% complementary to the full-length sequence of SEQ ID NO: 23 or 24.

9. A method for detecting at least two NDM1, KPC, IMP, VIM or OXA resistance-encoding genes in a sample, comprising:
   (a) contacting a sample suspected of containing at least two of the NDM1, KPC, IMP, VIM and OXA resistance-encoding genes with at least two primers having the formula:

$$5'-[X]_p-Y-3' \qquad (I),$$

wherein X is a 5' portion of each primer that is non-complementary to the NDM1, KPC, IMP, VIM and OXA resistance-encoding genes and Y is a 3' portion of each primer that is substantially complementary to at least a portion of one of the NDM1, KPC, IMP, VIM and OXA resistance-encoding genes, and p is 0 or 1, to produce a mixture;
   (b) incubating the mixture of step (a) under conditions sufficient to amplify NDM1, KPC, IMP, VIM and OXA target nucleic acids, thereby generating amplified target nucleic acids; and
   (c) detecting in a single reaction the amplified NDM1, KPC, IMP, VIM or OXA target nucleic acids using different fluorescence-generating probes for each target nucleic acid, wherein each different fluorescence-generating probe comprises a different fluorophore, and wherein each fluorescence-generating probe comprises a sequence that is at least 85% complementary to at least two of any of the full-length sequences selected from SEQ ID NO: 1, 4, 5, 6, 7, 13, 17, 20, 26, 27, 37, 38, 41, 42, 43, 48, 49, 54, 55, 60, 61, 64, 65, 68, 71, 74, 77, 78, 79, 80, 81, 82, and 83, wherein $R_a$ is a fluorophore with emission wavelength between about 400 and 900 nm, $R_b$ is a non-fluorescent quencher, and wherein substitution of $R_a$ and $R_b$ allows quenching of fluorescence when the probe is unhybridized.

10. The method of claim 9, wherein the amplified nucleic acids comprise at least a portion of at least two of the NDM1, KPC, IMP, VIM and OXA resistance-encoding genes.

11. The method of claim 9, wherein each primer comprises a sequence that is at least 85% complementary to at least one of any of the full-length sequences selected from SEQ ID NO: 2, 3, 8, 9, 10, 11, 12, 14, 15, 16, 18, 19, 21, 22, 34, 35, 36, 39, 40, 44, 45, 46, 47, 50, 51, 52, 53, 56, 57, 58, 59, 62, 63, 66, 67, 69, 70, 72, 73, 75, and 76.

12. The method of claim 9, wherein at least one fluorescence-generating probe further comprises a minor groove binder.

13. The method of claim 9, wherein X is [A-B]m and Y is [A-B]n, wherein A represents a sugar phosphate backbone, modified sugar phosphate backbone, locked nucleic acid backbone, or a variant thereof in any combination, B represents a nucleic acid base or a modified base, m and n are integers of from about 4 to about 30.

14. The method of claim 9, further comprising the step of amplifying a control nucleic acid having a sequence of SEQ ID NO: 33.

15. The method of claim 14, wherein the step of amplifying a control nucleic acid comprises using a fluorescence-generating probe that is at least 85% complementary to the full-length sequence of SEQ ID NO: 25, wherein $R_a$ is a fluorophore with emission wavelength between about 400 and 900 nm, $R_b$ is a non-fluorescent quencher, and wherein substitution of $R_a$ and $R_b$ allows quenching of fluorescence when the probe is unhybridized.

16. The method of claim 14, wherein the step of amplifying a control nucleic acid comprises using one or more primers that is at least 85% complementary to the full-length sequence of SEQ ID NO: 23 or 24.

17. The method of claim 9, wherein p is 1.

18. A method for simultaneously detecting NDM1, KPC, IMP, VIM and OXA nucleic acids in a sample, comprising:
(a) contacting a sample suspected of containing NDM1, KPC, IMP, VIM or OXA nucleic acids with:
(i) at least two forward flap primers, wherein each forward flap primer comprises at least one of the following full-length sequences:

```
                               (SEQ ID NO: 3)
aataaatcataaGCAGACTGGGCAGTCGG, (SEQ ID NO: 11)
aataaatAGGCAACCAAACCACTACGTTATCT, (SEQ ID NO: 12)
aataaatAGGCAGCCAAACTACTAGGTTATCT, (SEQ ID NO: 16)
aataaatcaCGAATGCGCAGCACCI*GGATAGA, (SEQ ID NO: 19)
aataaatcataaCGCCATCCCTGACGATCAAAC,
and (SEQ ID NO: 22)
aataaatcatTCTTGCCATTCCTTTGCTACCG,
``` wherein the lowercase nucleotide sequence is non-complementary to sequences of the NDM1, KPC, IMP, VIM or OXA nucleic acids; and
(ii) at least two reverse flap primers, wherein each reverse flap primer comprises at least one of the following full-length sequences:

```
                               (SEQ ID NO: 2)
aataaatcatGTCATTTGCCGTGCCATAC, (SEQ ID NO: 8)
aataaatcatGGAATA*GAGTGGCTTAATTCTC, (SEQ ID NO: 9)
aataaatcatGGAATA*GGGTGGCTTAATTCTC, (SEQ ID NO: 10)
aataaatcatGGAATA*GAATGGCTTAACTCTC, (SEQ ID NO: 14)
aataaCGCATTCTCTAGAAGGACTCTCATC, (SEQ ID NO: 15)
aataaCGCACTCTCTAAAAGCGCTCTCCTC, (SEQ ID NO: 18)
aataaatcataaGTCTGGCAGCACACTTCCTA,
and (SEQ ID NO: 21)
aataaatcaATGCGTGTATTAGCCTTATCGGC,
``` wherein the lowercase nucleotide sequence is non-complementary to sequences of the NDM1, KPC, IMP, VIM or OXA nucleic acids, to produce a reaction mixture;
(b) incubating the reaction mixture of step (a) under conditions sufficient to amplify the NDM1, KPC, IMP, VIM or OXA nucleic acids, thereby generating amplified nucleic acids; and
(c) detecting the amplified nucleic acids using at least two different fluorescence-generating probes, wherein the different fluorescence-generating probes comprise at least two different fluorophores, and wherein each fluorescence-generating probe comprises at least one of the following full-length sequences:

```
                                      (SEQ ID NO: 1)
R_{a1}-G*CAGGTTCCGGTTTTG-R_{b1}

(SEQ ID NO: 4)
R_{a2}-G*GI*CACACTCCAGATAAC-R_{b1}

(SEQ ID NO: 5)
R_{a2}-G*GI*CACACTCAAGATAAC-R_{b1}

(SEQ ID NO: 6)
R_{a2}-G*CTGA*A*TTAA*CI*AATGAGC-R_{b1}

(SEQ ID NO: 7)
R_{a2}-G*CTGA*A*TTAA*CI*AATGAAC-R_{b1}

(SEQ ID NO: 13)
R_{a2}-G*TGCGCTTCGGTCC-R_{b1}

(SEQ ID NO: 17)
R_{a2}-G*ACATGCCGGGTTTC-R_{b1}

(SEQ ID NO: 20)
R_{a3}-G*TGTTTTTGGTGGCATCG-R_{b1}

(SEQ ID NO: 26)
R_{a5}-G*GTGGCATCGATTATC-R_{b2}

(SEQ ID NO: 27)
R_{a6}-G*TGTTTTTGGTGGCATCG-R_{b3},
``` wherein $R_{a1}$, $R_{a2}$, $R_{a3}$, $R_{a5}$, and $R_{a6}$ are fluorophores with emission wavelengths between about 400 and 900 nm, $R_{b1}$, $R_{b2}$, and $R_{b3}$ are non-fluorescent quenchers, and wherein substitution of $R_a$ and $R_b$ allows quenching of fluorescence when the probe is unhybridized.

19. The method of claim 18, further comprising the step of amplifying a control nucleic acid having a sequence of SEQ ID NO: 33.

20. The method of claim 19, wherein the step of amplifying a control nucleic acid comprises using a fluorescence-generating probe that is at least 85% complementary to the full-length sequence of SEQ ID NO: 25 wherein $R_a$ is a fluorophore with emission wavelength between about 400 and 900 nm, $R_b$ is a non-fluorescent quencher, and wherein substitution of $R_a$ and $R_b$ allows quenching of fluorescence when the probe is unhybridized.

21. The method of claim 19, wherein the step of amplifying a control nucleic acid comprises using one or more primers that is at least 85% complementary to the full-length sequence of SEQ ID NO: 23 or 24.

22. A kit for detecting NDM1, KPC, IMP, VIM and OXA resistance-encoding genes in a sample, comprising one or more primers having a sequence that is at least 85% complementary to any of the full-length sequences selected from SEQ ID NO: 2, 3, 8, 9, 10, 11, 12, 14, 15, 16, 18, 19, 21, 22, 34, 35, 36, 39, 40, 44, 45, 46, 47, 50, 51, 52, 53, 56, 57, 58, 59, 62, 63, 66, 67, 69, 70, 72, 73, 75, and 76, and further comprising at least two different fluorescence-generating probes, wherein the different fluorescence-generating probes comprise at least two different fluorophores, and wherein each fluorescence-generating probe comprises a sequence that is at least 85% complementary to at least one of any of the full-length sequences selected from SEQ ID NO: 1, 4, 5, 6, 7, 13, 17, 20, 26, 27, 37, 38, 41, 42, 43, 48, 49, 54, 55, 60, 61, 64, 65, 68, 71, 74, 77, 78, 79, 80, 81, 82, and 83, wherein $R_a$ is a fluorophore with emission wavelength between about 400 and 900 nm, $R_b$ is a non-fluorescent quencher, and wherein substitution of $R_a$ and $R_b$ allows quenching of fluorescence when the probe is unhybridized.

23. The kit of claim 22, further comprising one or more primers or probes for amplifying a control nucleic acid having sequences that are at least 85% complementary to the full-length sequence of one or more of SEQ ID NO: 23, 24, or 25.

24. A kit for detecting NDM1, KPC, IMP, VIM and OXA resistance-encoding genes in a sample, comprising at least two different fluorescence-generating probes, wherein the different fluorescence-generating probes comprise at least two different fluorophores, and wherein each fluorescence-generating probe comprises a sequence that is at least 85% complementary to at least one of any of the full-length sequences selected from SEQ ID NO: 1, 4, 5, 6, 7, 13, 17, 20, 26, 27, 37, 38, 41, 42, 43, 48, 49, 54, 55, 60, 61, 64, 65, 68, 71, 74, 77, 78, 79, 80, 81, 82, and 83, wherein $R_a$ is a fluorophore with emission wavelength between about 400 and 900 nm, $R_b$ is a non-fluorescent quencher, and wherein substitution of $R_a$ and $R_b$ allows quenching of fluorescence when the probe is unhybridized.

25. The kit of claim 24, further comprising one or more primers comprising a sequence that is at least 85% complementary to any of the full-length sequences selected from SEQ ID NO: 2, 3, 8, 9, 10, 11, 12, 14, 15, 16, 18, 19, 21, 22, 34, 35, 36, 39, 40, 44, 45, 46, 47, 50, 51, 52, 53, 56, 57, 58, 59, 62, 63, 66, 67, 69, 70, 72, 73, 75, and 76.

26. The kit of claim 24, further comprising one or more primers or probes for amplifying a control nucleic acid having sequences that are at least 85% complementary to the full-length sequence of one or more of SEQ ID NO: 23, 24, or 25.

\* \* \* \* \*

SEQUENCE LISTING

```
<160> NUMBER OF SEQ ID NOS: 83

<210> SEQ ID NO 1
<211> LENGTH: 16
<212> TYPE: DNA
<213> ORGANISM: Artificial Sequence
<220> FEATURE:
<223> OTHER INFORMATION: KPC-FAM-1 probe
<220> FEATURE:
<221> NAME/KEY: m
<222> LOCATION: (1)..(1)
<223> OTHER INFORMATION: m is 6 amino 1H pyrazolo[3,4 d]pyrimidin 4(5H)
      one attached to FAM
<220> FEATURE:
<221> NAME/KEY: m
<222> LOCATION: (16)..(16)
<223> OTHER INFORMATION: m is Eclipse Dark Quencher attached to minor
      groove binder

<400> SEQUENCE: 1
mcaggttccg gttttm                                                        16

<210> SEQ ID NO 2
<211> LENGTH: 29
<212> TYPE: DNA
<213> ORGANISM: Artificial Sequence
<220> FEATURE:
<223> OTHER INFORMATION: KPC-L1 primer

<400> SEQUENCE: 2
aataaatcat gtcatttgcc gtgccatac                                          29

<210> SEQ ID NO 3
<211> LENGTH: 29
<212> TYPE: DNA
<213> ORGANISM: Artificial Sequence
<220> FEATURE:
<223> OTHER INFORMATION: KPC-E1 primer

<400> SEQUENCE: 3
```

```
aataaatcat aagcagactg ggcagtcgg                                            29
```

<210> SEQ ID NO 4
<211> LENGTH: 18
<212> TYPE: DNA
<213> ORGANISM: Artificial Sequence
<220> FEATURE:
<223> OTHER INFORMATION: IMP-AP593-4 probe
<220> FEATURE:
<221> NAME/KEY: m
<222> LOCATION: (1)..(1)
<223> OTHER INFORMATION: m is 6 amino 1H pyrazolo[3,4 d]pyrimidin 4(5H)
      one attached to AP593 dye
<220> FEATURE:
<221> NAME/KEY: m
<222> LOCATION: (3)..(3)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (18)..(18)
<223> OTHER INFORMATION: m is C attached to Eclipse Dark Quencher
      attached to minor groove binder

<400> SEQUENCE: 4

```
mgmcacactc cagataam                                                        18
```

<210> SEQ ID NO 5
<211> LENGTH: 18
<212> TYPE: DNA
<213> ORGANISM: Artificial Sequence
<220> FEATURE:
<223> OTHER INFORMATION: IMP-AP593-5 probe
<220> FEATURE:
<221> NAME/KEY: m
<222> LOCATION: (1)..(1)
<223> OTHER INFORMATION: m is 6 amino 1H pyrazolo[3,4 d]pyrimidin 4(5H)
      one attached to AP593 dye
<220> FEATURE:
<221> NAME/KEY: m
<222> LOCATION: (3)..(3)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (18)..(18)
<223> OTHER INFORMATION: m is C attached to Eclipse Dark Quencher
      attached to minor groove binder

<400> SEQUENCE: 5

```
mgmcacactc aagataam                                                        18
```

<210> SEQ ID NO 6
<211> LENGTH: 19
<212> TYPE: DNA
<213> ORGANISM: Artificial Sequence
<220> FEATURE:
<223> OTHER INFORMATION: IMP-AP593-15 probe
<220> FEATURE:
<221> NAME/KEY: m
<222> LOCATION: (1)..(1)
<223> OTHER INFORMATION: m is 6 amino 1H pyrazolo[3,4 d]pyrimidin 4(5H)
      one attached to AP593 dye
<220> FEATURE:
<221> NAME/KEY: m
<222> LOCATION: (5)..(6)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (10)..(10)
<223> OTHER INFORMATION: m is
      4-(4,6-Diamino-1H-pyrazolo[3,4-d]pyrimidin-3-yl)-but-3-yn-1-ol
<220> FEATURE:

<220> FEATURE:
<221> NAME/KEY: m
<222> LOCATION: (12)..(12)
<223> OTHER INFORMATION: m is
    3-aminobutynyl-1H-pyrazolo[3,4-d]pyrimidin-4(5H)-one
<220> FEATURE:
<221> NAME/KEY: m
<222> LOCATION: (19)..(19)
<223> OTHER INFORMATION: m is C attached to Eclipse Dark Quencher
    attached to minor groove binder

<400> SEQUENCE: 6
mctgmmttam cmaatgagm                                                19

<210> SEQ ID NO 7
<211> LENGTH: 19
<212> TYPE: DNA
<213> ORGANISM: Artificial Sequence
<220> FEATURE:
<223> OTHER INFORMATION: IMP-AP593-16 probe
<220> FEATURE:
<221> NAME/KEY: m
<222> LOCATION: (1)..(1)
<223> OTHER INFORMATION: m is
    6-amino-1H pyrazolo[3,4-d]pyrimidin-4(5H)-one attached to
    AP593 dye
<220> FEATURE:
<221> NAME/KEY: m
<222> LOCATION: (5)..(6)
<223> OTHER INFORMATION: m is
    4-(4,6-Diamino-1H-pyrazolo[3,4-d]pyrimidin-3-yl)-but-3-yn-1-ol
<220> FEATURE:
<221> NAME/KEY: m
<222> LOCATION: (10)..(10)
<223> OTHER INFORMATION: m is
    4-(4,6-Diamino-1H-pyrazolo[3,4-d]pyrimidin-3-yl)-but-3-yn-1-ol
<220> FEATURE:
<221> NAME/KEY: m
<222> LOCATION: (12)..(12)
<223> OTHER INFORMATION: m is
    3-aminobutynyl-1H-pyrazolo[3,4-d]pyrimidin-4(5H)-one
<220> FEATURE:
<221> NAME/KEY: m
<222> LOCATION: (19)..(19)
<223> OTHER INFORMATION: m is C attached to Eclipse Dark Quencher
    attached to minor groove binder

<400> SEQUENCE: 7
mctgmmttam cmaatgaam                                                19

<210> SEQ ID NO 8
<211> LENGTH: 32
<212> TYPE: DNA
<213> ORGANISM: Artificial Sequence
<220> FEATURE:
<223> OTHER INFORMATION: IMP-L1 primer
<220> FEATURE:
<221> NAME/KEY: m
<222> LOCATION: (16)..(16)
<223> OTHER INFORMATION: m is
    4-(4,6-Diamino-1H-pyrazolo[3,4-d]pyrimidin-3-yl)-but-3-yn-1-ol

<400> SEQUENCE: 8
aataaatcat ggaatmgagt ggcttaattc tc                                 32

<210> SEQ ID NO 9
<211> LENGTH: 32
<212> TYPE: DNA
<213> ORGANISM: Artificial Sequence
<220> FEATURE:
<223> OTHER INFORMATION: IMP-L2 primer
<220> FEATURE:
<221> NAME/KEY: m
<222> LOCATION: (16)..(16)

```
<223> OTHER INFORMATION: m is
      4-(4,6-Diamino-1H-pyrazolo[3,4-d]pyrimidin-3-yl)-but-3-yn-1-ol

<400> SEQUENCE: 9 ataaatcat ggaatmgggt ggcttaattc tc                                    32

<210> SEQ ID NO 10
<211> LENGTH: 32
<212> TYPE: DNA
<213> ORGANISM: Artificial Sequence
<220> FEATURE:
<223> OTHER INFORMATION: IMP-L3 primer
<220> FEATURE:
<221> NAME/KEY: m
<222> LOCATION: (16)..(16)
<223> OTHER INFORMATION: m is
      4-(4,6-Diamino-1H-pyrazolo[3,4-d]pyrimidin-3-yl)-but-3-yn-1-ol

<400> SEQUENCE: 10
aataaatcat ggaatmgaat ggcttaactc tc                                   32

<210> SEQ ID NO 11
<211> LENGTH: 32
<212> TYPE: DNA
<213> ORGANISM: Artificial Sequence
<220> FEATURE:
<223> OTHER INFORMATION: IMP-E7 primer

<400> SEQUENCE: 11
aataaatagg caaccaaacc actacgttat ct                                   32

<210> SEQ ID NO 12
<211> LENGTH: 32
<212> TYPE: DNA
<213> ORGANISM: Artificial Sequence
<220> FEATURE:
<223> OTHER INFORMATION: IMP-E8 primer

<400> SEQUENCE: 12
aataaatagg cagccaaact actaggttat ct                                   32

<210> SEQ ID NO 13
<211> LENGTH: 14
<212> TYPE: DNA
<213> ORGANISM: Artificial Sequence
<220> FEATURE:
<223> OTHER INFORMATION: VIM-AP593-7 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to AP593 dye
<220> FEATURE:
<221> NAME/KEY: m
<222> LOCATION: (14)..(14)
<223> OTHER INFORMATION: m is C attached to Eclipse Dark Quencher
      attached to minor groove binder

<400> SEQUENCE: 13
mtgcgcttcg gtcm                                                       14

<210> SEQ ID NO 14
<211> LENGTH: 30
<212> TYPE: DNA
<213> ORGANISM: Artificial Sequence
<220> FEATURE:
<223> OTHER INFORMATION: VIM-L4 primer

<400> SEQUENCE: 14
```
aataacgcat tctctagaag gactctcatc                                    30

<210> SEQ ID NO 15
<211> LENGTH: 30
<212> TYPE: DNA
<213> ORGANISM: Artificial Sequence
<220> FEATURE:
<223> OTHER INFORMATION: VIM-L6 primer

<400> SEQUENCE: 15
aataacgcac tctctaaaag cgctctcctc                                    30

<210> SEQ ID NO 16
<211> LENGTH: 32
<212> TYPE: DNA
<213> ORGANISM: Artificial Sequence
<220> FEATURE:
<223> OTHER INFORMATION: VIM-E6 primer
<220> FEATURE:
<221> NAME/KEY: m
<222> LOCATION: (25)..(25)
<223> OTHER INFORMATION: m is
      3-aminobutynyl-1H-pyrazolo[3,4-d]pyrimidin-4(5H)-one

<400> SEQUENCE: 16
aataaatcac gaatgcgcag caccmggata ga                                 32

<210> SEQ ID NO 17
<211> LENGTH: 15
<212> TYPE: DNA
<213> ORGANISM: Artificial Sequence
<220> FEATURE:
<223> OTHER INFORMATION: NDM-AP593-2 probe
<220> FEATURE:
<221> NAME/KEY: m
<222> LOCATION: (1)..(1)
<223> OTHER INFORMATION: m is
      6-amino-1H pyrazolo[3,4-d]pyrimidin-4(5H)-one attached to
      AP593 dye
<220> FEATURE:
<221> NAME/KEY: m
<222> LOCATION: (15)..(15)
<223> OTHER INFORMATION: m is C attached to Eclipse Dark Quencher
      attached to minor groove binder

<400> SEQUENCE: 17
macatgccgg gtttm                                                    15

<210> SEQ ID NO 18
<211> LENGTH: 32
<212> TYPE: DNA
<213> ORGANISM: Artificial Sequence
<220> FEATURE:
<223> OTHER INFORMATION: NDM-L2 primer

<400> SEQUENCE: 18
aataaatcat aagtctggca gcacacttcc ta                                 32

<210> SEQ ID NO 19
<211> LENGTH: 33
<212> TYPE: DNA
<213> ORGANISM: Artificial Sequence
<220> FEATURE:
<223> OTHER INFORMATION: NDM-E2 primer

<400> SEQUENCE: 19
aataaatcat aacgccatcc ctgacgatca aac                                33

<210> SEQ ID NO 20
<211> LENGTH: 18
<212> TYPE: DNA
<213> ORGANISM: Artificial Sequence
<220> FEATURE:
<223> OTHER INFORMATION: OXA-AP662-7 probe
<220> FEATURE:
<221> NAME/KEY: m
<222> LOCATION: (1)..(1)
<223> OTHER INFORMATION: m is
    6-amino-1H pyrazolo[3,4-d]pyrimidin-4(5H)-one attached to
    AP662 dye
<220> FEATURE:
<221> NAME/KEY: m
<222> LOCATION: (18)..(18)
<223> OTHER INFORMATION: m is G attached to Eclipse Dark Quencher
    attached to minor groove binder

<400> SEQUENCE: 20
mtgtttttgg tggcatcm                                              18

<210> SEQ ID NO 21
<211> LENGTH: 32
<212> TYPE: DNA
<213> ORGANISM: Artificial Sequence
<220> FEATURE:
<223> OTHER INFORMATION: OXA-L1 primer

<400> SEQUENCE: 21
aataaatcaa tgcgtgtatt agccttatcg gc                              32

<210> SEQ ID NO 22
<211> LENGTH: 32
<212> TYPE: DNA
<213> ORGANISM: Artificial Sequence
<220> FEATURE:
<223> OTHER INFORMATION: OXA-E1 primer

<400> SEQUENCE: 22
aataaatcat tcttgccatt cctttgctac cg                              32

<210> SEQ ID NO 23
<211> LENGTH: 23
<212> TYPE: DNA
<213> ORGANISM: Artificial Sequence
<220> FEATURE:
<223> OTHER INFORMATION: E6132-L primer

<400> SEQUENCE: 23
ctgcacggac cagttacttt acg                                        23

<210> SEQ ID NO 24
<211> LENGTH: 26
<212> TYPE: DNA
<213> ORGANISM: Artificial Sequence
<220> FEATURE:
<223> OTHER INFORMATION: E6132-E primer

<400> SEQUENCE: 24 ctcattttt ctaccggaga tcttgt                                      26

<210> SEQ ID NO 25
<211> LENGTH: 17
<212> TYPE: DNA
<213> ORGANISM: Artificial Sequence
<220> FEATURE:
<223> OTHER INFORMATION: E6132-AP525-TM3 probe
<220> FEATURE:

<220> FEATURE:
<221> NAME/KEY: m
<222> LOCATION: (1)..(1)
<223> OTHER INFORMATION: m is
    6-amino-1H pyrazolo[3,4-d]pyrimidin-4(5H)-one attached to
    AP525 dye
<220> FEATURE:
<221> NAME/KEY: m
<222> LOCATION: (17)..(17)
<223> OTHER INFORMATION: m is G attached to Eclipse Dark Quencher
    attached to minor groove binder

<400> SEQUENCE: 25
maccacgtac cgcattm                                                  17

<210> SEQ ID NO 26
<211> LENGTH: 16
<212> TYPE: DNA
<213> ORGANISM: Artificial Sequence
<220> FEATURE:
<223> OTHER INFORMATION: OXA-Ozr705-1 probe
<220> FEATURE:
<221> NAME/KEY: m
<222> LOCATION: (1)..(1)
<223> OTHER INFORMATION: m is 6-amino-1H
    pyrazolo[3,4-d]pyrimidin-4(5H)-one attached to Quasar 705 dye
<220> FEATURE:
<221> NAME/KEY: m
<222> LOCATION: (16)..(16)
<223> OTHER INFORMATION: m is C attached to
    (E)-4-((4-((2-chloro-4-nitrophenyl)diazenyl)-2,5-dimethoxyphenyl)
    (ethyl)amino)butanoic acid dye attached to minor groove binder

<400> SEQUENCE: 26
mgtggcatcg attatm                                                   16

<210> SEQ ID NO 27
<211> LENGTH: 18
<212> TYPE: DNA
<213> ORGANISM: Artificial Sequence
<220> FEATURE:
<223> OTHER INFORMATION: OXA-AP662-7 probe
<220> FEATURE:
<221> NAME/KEY: m
<222> LOCATION: (1)..(1)
<223> OTHER INFORMATION: m is 6-amino-1H
    pyrazolo[3,4-d]pyrimidin-4(5H)-one attached to AP622 dye attached
    to minor groove binder
<220> FEATURE:
<221> NAME/KEY: m
<222> LOCATION: (18)..(18)
<223> OTHER INFORMATION: m is G attached to Eclipse Dark Quencher

<400> SEQUENCE: 27 mtgttttgg tggcatcm                                                  18

<210> SEQ ID NO 28
<211> LENGTH: 12
<212> TYPE: DNA
<213> ORGANISM: Artificial Sequence
<220> FEATURE:
<223> OTHER INFORMATION: flap sequence of primer

<400> SEQUENCE: 28
aataaatcat aa                                                       12

<210> SEQ ID NO 29
<211> LENGTH: 10
<212> TYPE: DNA
<213> ORGANISM: Artificial Sequence
<220> FEATURE:
<223> OTHER INFORMATION: flap sequence of primer

```
<400> SEQUENCE: 29
aataaatcat                                                         10

<210> SEQ ID NO 30
<211> LENGTH: 9
<212> TYPE: DNA
<213> ORGANISM: Artificial Sequence
<220> FEATURE:
<223> OTHER INFORMATION: flap sequence of primer

<400> SEQUENCE: 30 aataaatca                                                           9

<210> SEQ ID NO 31
<211> LENGTH: 7
<212> TYPE: DNA
<213> ORGANISM: Artificial Sequence
<220> FEATURE:
<223> OTHER INFORMATION: flap sequence of primer

<400> SEQUENCE: 31 aataaat                                                             7

<210> SEQ ID NO 32
<211> LENGTH: 5
<212> TYPE: DNA
<213> ORGANISM: Artificial Sequence
<220> FEATURE:
<223> OTHER INFORMATION: flap sequence of primer

<400> SEQUENCE: 32 aataa                                                               5

<210> SEQ ID NO 33
<211> LENGTH: 68
<212> TYPE: DNA
<213> ORGANISM: Artificial Sequence
<220> FEATURE:
<223> OTHER INFORMATION: sequence for internal control

<400> SEQUENCE: 33
ctgcacggac cagttacttt acggaccacg taccgcattg gtacaagatc tccggtagaa    60
aaaatgag                                                            68

<210> SEQ ID NO 34
<211> LENGTH: 29
<212> TYPE: DNA
<213> ORGANISM: Artificial Sequence
<220> FEATURE:
<223> OTHER INFORMATION: KPC-E2 primer

<400> SEQUENCE: 34
aataaatcat aaacagcgag gccgtcatc                                     29

<210> SEQ ID NO 35
<211> LENGTH: 28
<212> TYPE: DNA
<213> ORGANISM: Artificial Sequence
<220> FEATURE:
<223> OTHER INFORMATION: KPC-L3 primer

<400> SEQUENCE: 35
aataaatcat aacccaatcc ctcgagcg                                      28
```

```
<210> SEQ ID NO 36
<211> LENGTH: 29
<212> TYPE: DNA
<213> ORGANISM: Artificial Sequence
<220> FEATURE:
<223> OTHER INFORMATION: KPC-L4 primer

<400> SEQUENCE: 36
aataaatcat aacccaatcc ctcgagcgc                                    29

<210> SEQ ID NO 37
<211> LENGTH: 15
<212> TYPE: DNA
<213> ORGANISM: Artificial Sequence
<220> FEATURE:
<223> OTHER INFORMATION: KPC-F2 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to FAM
<220> FEATURE:
<221> NAME/KEY: m
<222> LOCATION: (15)..(15)
<223> OTHER INFORMATION: m is G attached to Eclipse Dark Quencher and
      minor groove binder

<400> SEQUENCE: 37
mtctagccgc agcgm                                                   15

<210> SEQ ID NO 38
<211> LENGTH: 15
<212> TYPE: DNA
<213> ORGANISM: Artificial Sequence
<220> FEATURE:
<223> OTHER INFORMATION: KPC-F3 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to FAM
<220> FEATURE:
<221> NAME/KEY: m
<222> LOCATION: (15)..(15)
<223> OTHER INFORMATION: m is G attached to Eclipse Dark Quencher
      attached to minor groove binder

<400> SEQUENCE: 38
mtctagccgc agcgm                                                   15

<210> SEQ ID NO 39
<211> LENGTH: 31
<212> TYPE: DNA
<213> ORGANISM: Artificial Sequence
<220> FEATURE:
<223> OTHER INFORMATION: KPC-L5 primer

<400> SEQUENCE: 39
aataaatcat aacgggctga cggccttcat g                                 31

<210> SEQ ID NO 40
<211> LENGTH: 30
<212> TYPE: DNA
<213> ORGANISM: Artificial Sequence
<220> FEATURE:
<223> OTHER INFORMATION: KPC-E3 primer

<400> SEQUENCE: 40
aataaatcat aaagctccca gcggtccaga                                   30
```

<210> SEQ ID NO 41
<211> LENGTH: 16
<212> TYPE: DNA
<213> ORGANISM: Artificial Sequence
<220> FEATURE:
<223> OTHER INFORMATION: KPC-F4 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to FAM
<220> FEATURE:
<221> NAME/KEY: m
<222> LOCATION: (16)..(16)
<223> OTHER INFORMATION: m is G attached to Eclipse Dark Quencher
      attached to minor groove binder

<400> SEQUENCE: 41
mcgataccac gttccm                                                  16

<210> SEQ ID NO 42
<211> LENGTH: 17
<212> TYPE: DNA
<213> ORGANISM: Artificial Sequence
<220> FEATURE:
<223> OTHER INFORMATION: KPC-F5 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to FAM
<220> FEATURE:
<221> NAME/KEY: m
<222> LOCATION: (17)..(17)
<223> OTHER INFORMATION: m is A attached to Eclipse Dark Quencher
      attached to minor groove binder

<400> SEQUENCE: 42
mtggtatcgc cgatagm                                                 17

<210> SEQ ID NO 43
<211> LENGTH: 17
<212> TYPE: DNA
<213> ORGANISM: Artificial Sequence
<220> FEATURE:
<223> OTHER INFORMATION: KPC-F6 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to FAM attached to
      minor groove binder
<220> FEATURE:
<221> NAME/KEY: m
<222> LOCATION: (17)..(17)
<223> OTHER INFORMATION: m is G attached to Eclipse Dark Quencher

<400> SEQUENCE: 43
mgcgatacca cgttccm                                                 17

<210> SEQ ID NO 44
<211> LENGTH: 32
<212> TYPE: DNA
<213> ORGANISM: Artificial Sequence
<220> FEATURE:
<223> OTHER INFORMATION: IMP-L5 primer
<220> FEATURE:
<221> NAME/KEY: m
<222> LOCATION: (15)..(15)
<223> OTHER INFORMATION: m is
      3-aminobutynyl-1H-pyrazolo[3,4-d]pyrimidin-4(5H)-one

```
<220> FEATURE:
<221> NAME/KEY: m
<222> LOCATION: (27)..(27)
<223> OTHER INFORMATION: m is
      3-aminobutynyl-1H-pyrazolo[3,4-d]pyrimidin-4(5H)-one

<400> SEQUENCE: 44
gtttatgttc atacmtcgtt tgaagamgtt aa                                    32

<210> SEQ ID NO 45
<211> LENGTH: 32
<212> TYPE: DNA
<213> ORGANISM: Artificial Sequence
<220> FEATURE:
<223> OTHER INFORMATION: IMP-L6 primer
<220> FEATURE:
<221> NAME/KEY: m
<222> LOCATION: (15)..(15)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (27)..(27)
<223> OTHER INFORMATION: m is
      3-aminobutynyl-1H-pyrazolo[3,4-d]pyrimidin-4(5H)-one

<400> SEQUENCE: 45
gtttatgttc atacmtcgtt cgaagamgtt aa                                    32

<210> SEQ ID NO 46
<211> LENGTH: 32
<212> TYPE: DNA
<213> ORGANISM: Artificial Sequence
<220> FEATURE:
<223> OTHER INFORMATION: IMP-E5 primer
<220> FEATURE:
<221> NAME/KEY: m
<222> LOCATION: (22)..(22)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (25)..(25)
<223> OTHER INFORMATION: m is
      3-aminobutynyl-1H-pyrazolo[3,4-d]pyrimidin-4(5H)-one

<400> SEQUENCE: 46
aataaataca agaaccacca amccmtgttt ag                                    32

<210> SEQ ID NO 47
<211> LENGTH: 32
<212> TYPE: DNA
<213> ORGANISM: Artificial Sequence
<220> FEATURE:
<223> OTHER INFORMATION: IMP-E6 primer
<220> FEATURE:
<221> NAME/KEY: m
<222> LOCATION: (22)..(22)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (25)..(25)
<223> OTHER INFORMATION: m is
      3-aminobutynyl-1H-pyrazolo[3,4-d]pyrimidin-4(5H)-one

<400> SEQUENCE: 47
aataaataca agaaccacta amccmtgttt ag                                    32

<210> SEQ ID NO 48
<211> LENGTH: 16
```

```
<212> TYPE: DNA
<213> ORGANISM: Artificial Sequence
<220> FEATURE:
<223> OTHER INFORMATION: IMP-AP593-2 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to AP593 dye
<220> FEATURE:
<221> NAME/KEY: m
<222> LOCATION: (2)..(3)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (8)..(8)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (14)..(14)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (16)..(16)
<223> OTHER INFORMATION: m is C attached to Eclipse Dark Quencher
      attached to minor groove binder

<400> SEQUENCE: 48
mmmcaacmcc ccamcm                                                         16

<210> SEQ ID NO 49
<211> LENGTH: 15
<212> TYPE: DNA
<213> ORGANISM: Artificial Sequence
<220> FEATURE:
<223> OTHER INFORMATION: IMP-AP593-7 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to AP593 dye attached
      to minor groove binder
<220> FEATURE:
<221> NAME/KEY: m
<222> LOCATION: (3)..(3)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (7)..(7)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (11)..(11)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (14)..(14)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (15)..(15)
<223> OTHER INFORMATION: m is T attached to Eclipse Dark Quencher

<400> SEQUENCE: 49
mgmcacmctc magmm                                                          15

<210> SEQ ID NO 50
<211> LENGTH: 32
```

```
<212> TYPE: DNA
<213> ORGANISM: Artificial Sequence
<220> FEATURE:
<223> OTHER INFORMATION: IMP-L7 primer
<220> FEATURE:
<221> NAME/KEY: m
<222> LOCATION: (3)..(3)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (6)..(6)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (9)..(9)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (27)..(27)
<223> OTHER INFORMATION: m is
      3-aminobutynyl-1H-pyrazolo[3,4-d]pyrimidin-4(5H)-one

<400> SEQUENCE: 50
aamaamaama ttgaagtttt ttatccmggc cc                           32

<210> SEQ ID NO 51
<211> LENGTH: 32
<212> TYPE: DNA
<213> ORGANISM: Artificial Sequence
<220> FEATURE:
<223> OTHER INFORMATION: IMP-L8 primer
<220> FEATURE:
<221> NAME/KEY: m
<222> LOCATION: (15)..(15)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (18)..(18)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (21)..(21)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (26)..(26)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (28)..(28)
<223> OTHER INFORMATION: m is
      3-aminobutynyl-1H-pyrazolo[3,4-d]pyrimidin-4(5H)-one

<400> SEQUENCE: 51
tattggctag ttaamaamaa mattgmamtt tt                           32

<210> SEQ ID NO 52
<211> LENGTH: 32
<212> TYPE: DNA
<213> ORGANISM: Artificial Sequence
<220> FEATURE:
<223> OTHER INFORMATION: IMP-E7 primer

<400> SEQUENCE: 52
aataaatagg caaccaaacc actacgttat ct                           32
```

```
<210> SEQ ID NO 53
<211> LENGTH: 32
<212> TYPE: DNA
<213> ORGANISM: Artificial Sequence
<220> FEATURE:
<223> OTHER INFORMATION: IMP-E8 primer

<400> SEQUENCE: 53
aataaatagg cagccaaact actaggttat ct                                    32

<210> SEQ ID NO 54
<211> LENGTH: 15
<212> TYPE: DNA
<213> ORGANISM: Artificial Sequence
<220> FEATURE:
<223> OTHER INFORMATION: IMP-AP593-3 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to AP593 dye
<220> FEATURE:
<221> NAME/KEY: m
<222> LOCATION: (3)..(3)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (5)..(5)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (7)..(7)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (11)..(11)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (15)..(15)
<223> OTHER INFORMATION: m is T attached to Eclipse Dark Quencher
      attached to minor groove binder

<400> SEQUENCE: 54
mgmcmcmctc magam                                                       15

<210> SEQ ID NO 55
<211> LENGTH: 15
<212> TYPE: DNA
<213> ORGANISM: Artificial Sequence
<220> FEATURE:
<223> OTHER INFORMATION: IMP-AP593-7
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to AP593 dye attached
      to minor groove binder
<220> FEATURE:
<221> NAME/KEY: m
<222> LOCATION: (3)..(3)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (7)..(7)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (11)..(11)
```

```
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (14)..(14)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (15)..(15)
<223> OTHER INFORMATION: m is T attached to minor groove binder

<400> SEQUENCE: 55
mgmcacmctc magmm                                                  15

<210> SEQ ID NO 56
<211> LENGTH: 32
<212> TYPE: DNA
<213> ORGANISM: Artificial Sequence
<220> FEATURE:
<223> OTHER INFORMATION: VIM-L3 primer
<220> FEATURE:
<221> NAME/KEY: m
<222> LOCATION: (16)..(16)
<223> OTHER INFORMATION: m is
      4-(4,6-Diamino-1H-pyrazolo[3,4-d]pyrimidin-3-yl)-but-3-yn-1-ol

<400> SEQUENCE: 56
aataaatcat aaggcmcttc tcgcggagat tg                               32

<210> SEQ ID NO 57
<211> LENGTH: 31
<212> TYPE: DNA
<213> ORGANISM: Artificial Sequence
<220> FEATURE:
<223> OTHER INFORMATION: VIM-E2 primer

<400> SEQUENCE: 57
aataaatcat aagacgcggt cgtcatgaaa g                                31

<210> SEQ ID NO 58
<211> LENGTH: 31
<212> TYPE: DNA
<213> ORGANISM: Artificial Sequence
<220> FEATURE:
<223> OTHER INFORMATION: VIM-E3 primer
<220> FEATURE:
<221> NAME/KEY: m
<222> LOCATION: (19)..(19)
<223> OTHER INFORMATION: m is
      3-aminobutynyl-1H-pyrazolo[3,4-d]pyrimidin-4(5H)-one
<220> FEATURE:
<221> NAME/KEY: m
<222> LOCATION: (28)..(28)
<223> OTHER INFORMATION: m is
      3-aminobutynyl-1H-pyrazolo[3,4-d]pyrimidin-4(5H)-one

<400> SEQUENCE: 58
aataaatcat aagacgcgmt cgtcatgmaa g                                31

<210> SEQ ID NO 59
<211> LENGTH: 32
<212> TYPE: DNA
<213> ORGANISM: Artificial Sequence
<220> FEATURE:
<223> OTHER INFORMATION: VIM-E4 primer
<220> FEATURE:
<221> NAME/KEY: m
<222> LOCATION: (24)..(24)
<223> OTHER INFORMATION: m is
      3-aminobutynyl-1H-pyrazolo[3,4-d]pyrimidin-4(5H)-one
```

<400> SEQUENCE: 59
aataaatcat acgtggagac tgcmcgcgtt ac                                      32

<210> SEQ ID NO 60
<211> LENGTH: 18
<212> TYPE: DNA
<213> ORGANISM: Artificial Sequence
<220> FEATURE:
<223> OTHER INFORMATION: VIM-AP593-2 probe
<220> FEATURE:
<221> NAME/KEY: m
<222> LOCATION: (1)..(1)
<223> OTHER INFORMATION: m is
      6-amino-1H pyrazolo[3,4-d]pyrimidin-4(5H)-one attached to
      AP593 dye
<220> FEATURE:
<221> NAME/KEY: m
<222> LOCATION: (18)..(18)
<223> OTHER INFORMATION: m is C attached to Eclipse Dark Quencher
      attached to minor groove binder

<400> SEQUENCE: 60
maagcaaatt ggacttcm                                                      18

<210> SEQ ID NO 61
<211> LENGTH: 18
<212> TYPE: DNA
<213> ORGANISM: Artificial Sequence
<220> FEATURE:
<223> OTHER INFORMATION: VIM-AP593-4 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to AP593 dye attached
      to minor groove binder
<220> FEATURE:
<221> NAME/KEY: m
<222> LOCATION: (18)..(18)
<223> OTHER INFORMATION: m is C attached to Eclipse Dark Quencher

<400> SEQUENCE: 61
maagcaaatt ggmcttcm                                                      18

<210> SEQ ID NO 62
<211> LENGTH: 30
<212> TYPE: DNA
<213> ORGANISM: Artificial Sequence
<220> FEATURE:
<223> OTHER INFORMATION: VIM-L4 primer

<400> SEQUENCE: 62
aataacgcat tctctagaag gactctcatc                                         30

<210> SEQ ID NO 63
<211> LENGTH: 32
<212> TYPE: DNA
<213> ORGANISM: Artificial Sequence
<220> FEATURE:
<223> OTHER INFORMATION: VIM-E5 primer
<220> FEATURE:
<221> NAME/KEY: m
<222> LOCATION: (23)..(23)
<223> OTHER INFORMATION: m is
      3-aminobutynyl-1H-pyrazolo[3,4-d]pyrimidin-4(5H)-one

<400> SEQUENCE: 63
aataaatcat atgcgcagca ccmggataga ag                                      32

<210> SEQ ID NO 64
<211> LENGTH: 17
<212> TYPE: DNA
<213> ORGANISM: Artificial Sequence
<220> FEATURE:
<223> OTHER INFORMATION: VIM-AP593-3 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to AP593 dye
<220> FEATURE:
<221> NAME/KEY: m
<222> LOCATION: (17)..(17)
<223> OTHER INFORMATION: m is G attached to Eclipse Dark Quencher
      attached to minor groove binder

<400> SEQUENCE: 64
mcgcttcggt ccagtam                                                      17

<210> SEQ ID NO 65
<211> LENGTH: 17
<212> TYPE: DNA
<213> ORGANISM: Artificial Sequence
<220> FEATURE:
<223> OTHER INFORMATION: VIM-AP593-6 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to AP593 dye attached
      to minor groove binder
<220> FEATURE:
<221> NAME/KEY: m
<222> LOCATION: (16)..(16)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (17)..(17)
<223> OTHER INFORMATION: m is G attached to Eclipse Dark Quencher

<400> SEQUENCE: 65
mcgcttcggt ccagtmm                                                      17

<210> SEQ ID NO 66
<211> LENGTH: 32
<212> TYPE: DNA
<213> ORGANISM: Artificial Sequence
<220> FEATURE:
<223> OTHER INFORMATION: NDM-L2 primer

<400> SEQUENCE: 66
aataaatcat aagtctggca gcacacttcc ta                                     32

<210> SEQ ID NO 67
<211> LENGTH: 33
<212> TYPE: DNA
<213> ORGANISM: Artificial Sequence
<220> FEATURE:
<223> OTHER INFORMATION: NDM-E2 primer

<400> SEQUENCE: 67
aataaatcat aacgccatcc ctgacgatca aac                                    33

<210> SEQ ID NO 68
<211> LENGTH: 15
<212> TYPE: DNA
<213> ORGANISM: Artificial Sequence
<220> FEATURE:

```
<223> OTHER INFORMATION: NDM-AP593-2 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to AP593 dye
<220> FEATURE:
<221> NAME/KEY: m
<222> LOCATION: (15)..(15)
<223> OTHER INFORMATION: m is C attached to Eclipse Dark Quencher
      attached to minor groove binder

<400> SEQUENCE: 68
macatgccgg gtttm                                                        15

<210> SEQ ID NO 69
<211> LENGTH: 31
<212> TYPE: DNA
<213> ORGANISM: Artificial Sequence
<220> FEATURE:
<223> OTHER INFORMATION: NDM-L3 primer
<220> FEATURE:
<221> NAME/KEY: m
<222> LOCATION: (26)..(26)
<223> OTHER INFORMATION: m is
      3-aminobutynyl-1H-pyrazolo[3,4-d]pyrimidin-4(5H)-one

<400> SEQUENCE: 69
aataaatcat aataccgcct ggaccmatga c                                      31

<210> SEQ ID NO 70
<211> LENGTH: 31
<212> TYPE: DNA
<213> ORGANISM: Artificial Sequence
<220> FEATURE:
<223> OTHER INFORMATION: NDM-E3 primer

<400> SEQUENCE: 70
aataaatcat aaaccggcag gttgatctcc t                                      31

<210> SEQ ID NO 71
<211> LENGTH: 17
<212> TYPE: DNA
<213> ORGANISM: Artificial Sequence
<220> FEATURE:
<223> OTHER INFORMATION: NDM-AP593-3 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to AP593 dye
<220> FEATURE:
<221> NAME/KEY: m
<222> LOCATION: (17)..(17)
<223> OTHER INFORMATION: m is G attached to Eclipse Dark Quencher
      attached to minor groove binder

<400> SEQUENCE: 71
mcccagatcc tcaactm                                                      17

<210> SEQ ID NO 72
<211> LENGTH: 30
<212> TYPE: DNA
<213> ORGANISM: Artificial Sequence
<220> FEATURE:
<223> OTHER INFORMATION: OXA-E2 primer

<400> SEQUENCE: 72
aataaatcat aaaaacgggc gaaccaagca                                        30
```

<210> SEQ ID NO 73
<211> LENGTH: 32
<212> TYPE: DNA
<213> ORGANISM: Artificial Sequence
<220> FEATURE:
<223> OTHER INFORMATION: OXA-E3 primer

<400> SEQUENCE: 73
aataaatcat aacgcgtctg tccatcccac tt                                32

<210> SEQ ID NO 74
<211> LENGTH: 19
<212> TYPE: DNA
<213> ORGANISM: Artificial Sequence
<220> FEATURE:
<223> OTHER INFORMATION: OXA-AP662-2 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to AP662 dye
<220> FEATURE:
<221> NAME/KEY: m
<222> LOCATION: (12)..(15)
<223> OTHER INFORMATION: m is
      5-(4-hydroxy-but-1-ynyl)-1H-pyrimidine-2,4-dione
<220> FEATURE:
<221> NAME/KEY: m
<222> LOCATION: (19)..(19)
<223> OTHER INFORMATION: m is G attached to Eclipse Dark Quencher
      attached to minor groove binder

<400> SEQUENCE: 74
mctattggga ammmmaaam                                               19

<210> SEQ ID NO 75
<211> LENGTH: 32
<212> TYPE: DNA
<213> ORGANISM: Artificial Sequence
<220> FEATURE:
<223> OTHER INFORMATION: OXA-L3 primer

<400> SEQUENCE: 75
aataaatcat accgaagcca atggtgacta ta                                32

<210> SEQ ID NO 76
<211> LENGTH: 32
<212> TYPE: DNA
<213> ORGANISM: Artificial Sequence
<220> FEATURE:
<223> OTHER INFORMATION: OXA-E3 primer
<220> FEATURE:
<221> NAME/KEY: m
<222> LOCATION: (13)..(13)
<223> OTHER INFORMATION: m is
      3-aminobutynyl-1H-pyrazolo[3,4-d]pyrimidin-4(5H)-one

<400> SEQUENCE: 76
aataaatcaa ccmacccacc agccaatctt ag                                32

<210> SEQ ID NO 77
<211> LENGTH: 18
<212> TYPE: DNA
<213> ORGANISM: Artificial Sequence
<220> FEATURE:
<223> OTHER INFORMATION: OXA-AP662-3 probe
<220> FEATURE:
<221> NAME/KEY: m
<222> LOCATION: (1)..(1)
<223> OTHER INFORMATION: m is 6-amino-1H

```
        pyrazolo[3,4-d]pyrimidin-4(5H)-one attached to AP662 dye
<220> FEATURE:
<221> NAME/KEY: m
<222> LOCATION: (10)..(10)
<223> OTHER INFORMATION: m is
        3-aminobutynyl-1H-pyrazolo[3,4-d]pyrimidin-4(5H)-one
<220> FEATURE:
<221> NAME/KEY: m
<222> LOCATION: (18)..(18)
<223> OTHER INFORMATION: m is C attached to Eclipse Dark Quencher
        attached to minor groove binder

<400> SEQUENCE: 77
mgctaaaacm ggatactm                                                 18

<210> SEQ ID NO 78
<211> LENGTH: 18
<212> TYPE: DNA
<213> ORGANISM: Artificial Sequence
<220> FEATURE:
<223> OTHER INFORMATION: OXA-AP662-6 probe
<220> FEATURE:
<221> NAME/KEY: m
<222> LOCATION: (1)..(1)
<223> OTHER INFORMATION: m is 6-amino-1H
        pyrazolo[3,4-d]pyrimidin-4(5H)-one attached to AP662 dye attached
        to minor groove binder
<220> FEATURE:
<221> NAME/KEY: m
<222> LOCATION: (9)..(9)
<223> OTHER INFORMATION: m
        is 3-aminobutynyl-1H-pyrazolo[3,4-d]pyrimidin-4(5H)-one
<220> FEATURE:
<221> NAME/KEY: m
<222> LOCATION: (14)..(14)
<223> OTHER INFORMATION: m is
        4-(4,6-Diamino-1H-pyrazolo[3,4-d]pyrimidin-3-yl)-but-3-yn-1-ol
<220> FEATURE:
<221> NAME/KEY: m
<222> LOCATION: (18)..(18)
<223> OTHER INFORMATION: m is G attached to Eclipse Dark Quencher

<400> SEQUENCE: 78
mctaaaacmg gatmctcm                                                 18

<210> SEQ ID NO 79
<211> LENGTH: 19
<212> TYPE: DNA
<213> ORGANISM: Artificial Sequence
<220> FEATURE:
<223> OTHER INFORMATION: OXA-PBI1 probe
<220> FEATURE:
<221> NAME/KEY: m
<222> LOCATION: (1)..(1)
<223> OTHER INFORMATION: m is 6-amino-1H
        pyrazolo[3,4-d]pyrimidin-4(5H)-one attached to AP662 dye and
        minor groove binder
<220> FEATURE:
<221> NAME/KEY: m
<222> LOCATION: (19)..(19)
<223> OTHER INFORMATION: m is A attached to Eclipse Dark Quencher

<400> SEQUENCE: 79
mataatcgat gccaccaam                                                19

<210> SEQ ID NO 80
<211> LENGTH: 19
<212> TYPE: DNA
<213> ORGANISM: Artificial Sequence
<220> FEATURE:
<223> OTHER INFORMATION: OXA-PBI2 probe
<220> FEATURE:
<221> NAME/KEY: m
```

```
<222> LOCATION: (1)..(1)
<223> OTHER INFORMATION: m is 6-amino-1H
      pyrazolo[3,4-d]pyrimidin-4(5H)-one attached to AP662 dye attached
      to minor groove binder
<220> FEATURE:
<221> NAME/KEY: m
<222> LOCATION: (19)..(19)
<223> OTHER INFORMATION: m is A attached to Eclipse Dark Quencher

<400> SEQUENCE: 80
mataatcgat gccaccaam                                                    19

<210> SEQ ID NO 81
<211> LENGTH: 19
<212> TYPE: DNA
<213> ORGANISM: Artificial Sequence
<220> FEATURE:
<223> OTHER INFORMATION: OXA-PBI3 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to AP680 dye attached
      to minor groove binder
<220> FEATURE:
<221> NAME/KEY: m
<222> LOCATION: (19)..(19)
<223> OTHER INFORMATION: m is A attached to Eclipse Dark Quencher

<400> SEQUENCE: 81
mataatcgat gccaccaam                                                    19

<210> SEQ ID NO 82
<211> LENGTH: 19
<212> TYPE: DNA
<213> ORGANISM: Artificial Sequence
<220> FEATURE:
<223> OTHER INFORMATION: OXA-PBI4 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attahced to AP680 dye attached
      to minor groove binder
<220> FEATURE:
<221> NAME/KEY: m
<222> LOCATION: (19)..(19)
<223> OTHER INFORMATION: m is A attached to Eclipse Dark Quencher

<400> SEQUENCE: 82
mataatcgat gccaccaam                                                    19

<210> SEQ ID NO 83
<211> LENGTH: 16
<212> TYPE: DNA
<213> ORGANISM: Artificial Sequence
<220> FEATURE:
<223> OTHER INFORMATION: OXA-Cy55-1 probe
<220> FEATURE:
<221> NAME/KEY: m
<222> LOCATION: (1)..(1)
<223> OTHER INFORMATION: m is 6-amino-1H
      pyrazolo[3,4-d]pyrimidin-4(5H)-one attached to Cy5.5 dye
<220> FEATURE:
<221> NAME/KEY: m
<222> LOCATION: (16)..(16)
<223> OTHER INFORMATION: m is C attached to Eclipse Dark Quencher
      attached to minor groove binder

<400> SEQUENCE: 83
mgtggcatcg attatm                                                       16
```